US010024844B2

(12) United States Patent
Blobel et al.

(10) Patent No.: US 10,024,844 B2
(45) Date of Patent: Jul. 17, 2018

(54) IDENTIFICATION OF AN INHIBITOR OF IRHOM1 OR AN INHIBITOR OF IRHOM2

(71) Applicants: Hospital for Special Surgery, New York, NY (US); University Health Network, Toronto (CA)

(72) Inventors: Carl Blobel, New York, NY (US); Thorsten Maretzky, New York, NY (US); David McIlwain, Toronto (CA); Tak Wah Mak, Toronto (CA)

(73) Assignees: Hospital for Special Surgery, New York, NY (US); University Health Network, Toronto (CA)

( * ) Notice: Subject to any disclaimer, the term of this patent is extended or adjusted under 35 U.S.C. 154(b) by 0 days.

(21) Appl. No.: 14/654,139

(22) PCT Filed: Dec. 20, 2013

(86) PCT No.: PCT/US2013/076954
§ 371 (c)(1),
(2) Date: Jun. 19, 2015

(87) PCT Pub. No.: WO2014/100602
PCT Pub. Date: Jun. 26, 2014

(65) Prior Publication Data
US 2015/0316538 A1 Nov. 5, 2015

Related U.S. Application Data

(60) Provisional application No. 61/740,226, filed on Dec. 20, 2012.

(51) Int. Cl.
*G01N 33/48* (2006.01)
*G01N 33/50* (2006.01)
*A61K 39/395* (2006.01)
*A61K 45/06* (2006.01)
*C07K 16/18* (2006.01)
*C12N 15/113* (2010.01)
*A61K 39/00* (2006.01)

(52) U.S. Cl.
CPC ..... *G01N 33/5032* (2013.01); *A61K 39/3955* (2013.01); *A61K 45/06* (2013.01); *C07K 16/18* (2013.01); *C12N 15/113* (2013.01); *A61K 2039/507* (2013.01); *C12N 2310/14* (2013.01); *G01N 2500/02* (2013.01)

(58) Field of Classification Search
None
See application file for complete search history.

(56) References Cited

U.S. PATENT DOCUMENTS 7,718,391 B2 * 5/2010 Freeman .............. C12N 9/6424
2006/0240425 A1 * 10/2006 Nakamura ............ C07K 14/47

OTHER PUBLICATIONS

Calafat et al., Human monocytes and neutrophils store transforming growth factor-alpha in a subpopulation of cytoplasmic granules, Blood, 90(3):1255-1266, 1997.*
Elovic et al., IL-4-dependent regulation of TGF-alph and TGF-beta1 expression in human eosinophils, J. Immunol. 160:6121-6127, 1998.*
Yan et al. "Human rhomboid family-1 gene silencing causes apoptosis or autophagy to epithelial cancer cells and inhibits xenograft tumor growth." Mol. Cancer Ther. 2008, col. 7, No. 6, pp. 1355-1364.
Zou et al. "Human rhomboid family-1 gene RHBDF1 participates in GPCR-mediated transactivation of EGFR growth signals in head and neck squamous cancer cells." FASEB J. 2009, vol. 23, No. 2, pp. 425-432.
He et al. "Inhibition of human squamous cell carcinoma growth in vivo by epidermal growth factor receptor antisense RNA transcribed from THEU6 promoter." J. Nat. Cancer Instit. 1998, vol. 90, No. 14, pp. 1080-1087.
Andrain et al. "Tumor necrosis factor requires iRhom2 to Promote Trafflixking and Activation of TACE." Science 2012, vol. 335, No. 6065, pp. 225-228.
Maretzky et al. "iRhom2 controls substrate selectivity pf stimulated ADAM17-dependent ectodomain shedding." PNAS 2013, vol. 110, No. 28, pp. 11433-11438.
Lichtenthaler "iRhom2 takes control of rheumatoid arthritis." J. Clin. Investig. 2013, vol. 12, No. 2, pp. 560-562.
Darshinee al. "iRhom2 is a critical pathogenic mediator of inflammatory arthritis." J. Clin. Investig. 2013, vol. 123, No. 2., pp. 928-932.
Written Opinion of the International Search Authority for PCT/US2013/076954, dated Apr. 10, 2014, 9 pages.
International Search Report for PCT/US2013/076954, published Jun. 6, 2014, 5 pages.
Horiuchi, K, Kimura, T., Miyamoto, T., Takaishi, H., Okada, Y., Toyama, Y., and Blobel, C.P. 2007. Cutting Edge: TNF-α-Converting Enzyme (TACE/ADAMI7) Inactivation in Mouse Myeloid Cells Prevents Lethality from Endotoxin Shock. J Immunol 179:2686-2689.
Kuan CT, Wikstrand CJ, Bigner DD (Jun. 2001), (EGF mutant receptor vIII as a molecular target in cancer therapy, Endocr. Relat. Cancer 8 (2): 83-96.
Le Gall, et al., "ADAM 17 is Regulated by a Rapid and Reversible Mechanism that Controls Access to its Catalytic Site", Journal of Cell Science, 123:3913 (2010).

(Continued)

*Primary Examiner* — Claire Kaufman
(74) *Attorney, Agent, or Firm* — McCarter & English, LLP; Steven G. Davis; Mei Bai

(57) ABSTRACT

Disclosed are methods for treating a subject with an EGFR dependent pathology. The method comprises the step of administering to the subject an effective amount of an agent ("First Agent") that decreases the biological activity of iRhom1 and an effective amount of an agent ("Second Agent") that decreases the biological activity of iRhom2. Alternatively, the method comprises the step of administering to the subject an effective amount of an agent ("First Agent") that modulates formation of a complex between iRhom 1 and TACE and an effective amount of an agent ("Second Agent") that modulates formation of a complex between TACE and iRhom2. Also disclosed are assays for identifying such agents.

4 Claims, 3 Drawing Sheets

(56) References Cited

OTHER PUBLICATIONS

Le Gall, et al., "ADAMs 10 and 17 Represent Differentially Regulated Components of a General Shedding Machinery or Membrane Proteins Such as Transforming Growth Factor ?, L-Selectin, and Tumor Necrosis Factor ?", Molecular Biology of the Cell, 20:1785 (2009).

McIlwain, D.R., Lang, P.A., Maretzky, T., Hamada, K., Ohishi, K., Maney, S.K., Berger, T., Murthy, A., Duncan, G., Xu, H.C., et al. 2012. iRhom2 regulation of TACE controls TNF-mediated protection against Listeria and responses to LPS. Science 335:229-232.

Oda K, Matsuoka Y, Funahashi A, Kitano H (2005), "A comprehensive pathway map of epidermal growth factor receptor signaling". Mol. Syst. Biol. 1 (1): 2005.0010.

Peschon, J.J., Slack, J.L., Reddy, P., Stocking, K.L., Sunnarborg, S.W., Lee, D.C., Russel, W.E., Castner, B.J., Johnson, R.S., Fitzner, J.N., et al. 1998. An essential role for ectodomain shedding in mammalian development. Science 282:1281-1284.

Sahin et al., "Distinct Roles for ADAM10 and ADAM 17 in Ectodomain Shedding of six EGFR Ligands" The Journal of Cell Biology, 164:769 (2004).

Sahin, et al., "Ectodomain shedding of the EGF-Receptor Ligand Epigen is Mediated by ADAM17", FEBS, 581:41 (2007).

Siggs, O.M., Xiao, N., Wang, Y., Shi, H., Tomisato, W., Li, X., Xia, Y., and Beutler, B. 2012. iRhom2 is required for the secretion of mouse TNF?. Blood 119:5769-5771.

Walker F, Abramowitz L, Benabderrahmane D, Duval X, Descatoire V, Hénin D, Lehy T, Aparicio T (Nov. 2009), "Growth factor receptor expression in anal squamous lesions: modifications associated with oncogenic human papillomavirus and human immunodeficiency virus", Hum. Pathol. 40 (11): 1517-27.

Yosef Yarden and Joseph Schlessinger (1987), "Epidermal Growth-Factor Induces Rapid, Reversible Aggregation of the Purified Epidermal Growth-Factor Receptor", Biochemistry 26 (5): 1443-1451.

Zhang H, Berezov A, Wang Q, Zhang G, Drebin J, Murali R, Greene MI (Aug. 2007). "ErbB receptors: from oncogenes to targeted cancer therapies". J. Clin. Invest. 117 (8): 2051-8.

Li, et al., Proc Natl Acad Sci U S A. 2015,112(19): 6080-5.

Maretzky, et al., Proc Natl Acad Sci U S A. 2013, 110(28):11433-8.

* cited by examiner

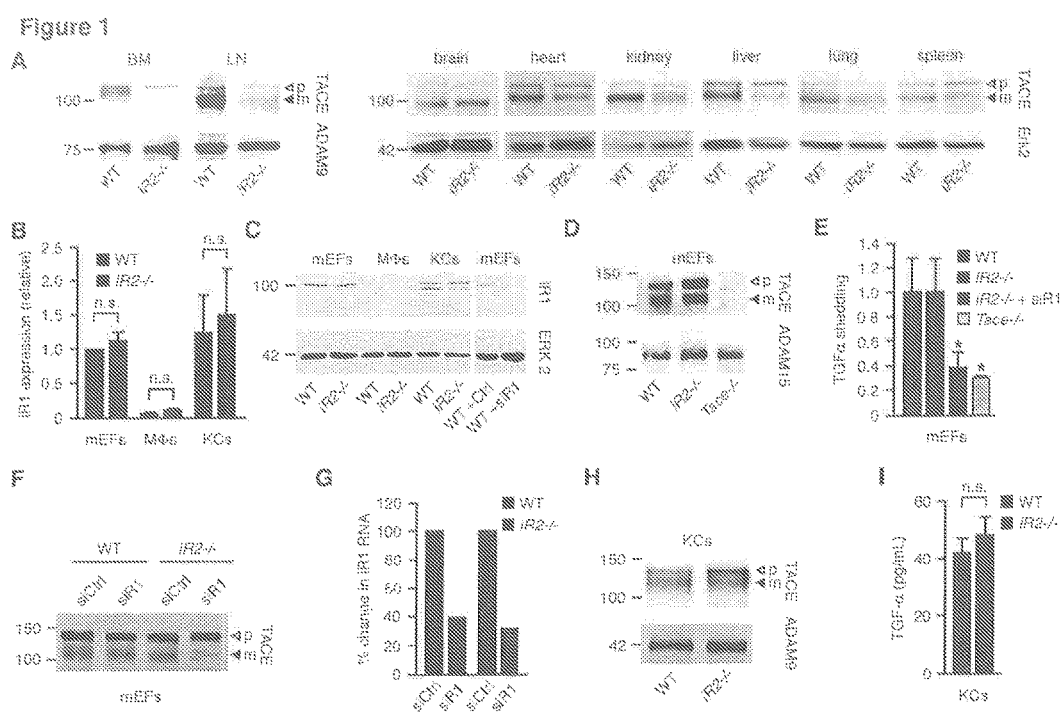

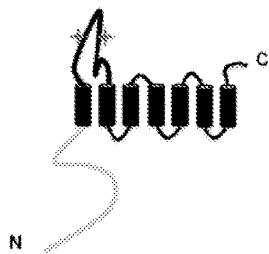

MASADKNGSNLPSVSGSRLQSRKPPNLSITIPPPESQAPGEQDSMLPERRKNPAYLKSVSLQEPRGRWQE
GAEKRPGFRRQASLSQSIRKSTAQWFGVSGDWEGKRQNWHRRSLHHCSVHYGRLKASCQRELELPSQEVP
SFQGTESPKPCKMPKIVDPLARGRAFRHPDEVDRPHAAHPPLIPGVLSLTSFTSVRSGYSHLPRRKRISV
AHMSFQAAAALLKGRSVLDATGQRCRHVKRSFAYPSFLEEDAVDGADTFDSSFFSKEEMSSMPDDVFESP
PLSASYFRGVPHSASPVSPDGVHIPLKEYSGGRALGPGTQRGKRIASKVKHFAFDRKKRHYGLGVVGNWL
NRSYRRSISSTVQRQLESFDSHRPYFTYWLTFVHIIITLLVICTYGIAPVGFAQHVTTQLVLKNRGVYES
VKYIQQENFWIGPSSIDLIHLGAKFSP█IRKDQQIEQLVRRERDIERTSG█VQNDRSG█IQTLKKD█SE
TLATFVKWQ███GPSDKSDLSQKQPSAVV█HQDPRT█EEPASSGAHIWPDDITKWPI█TEQAQS███GLL
HID█KIKGRP█IGTKGS█EITTREY█EFMHGYFHEDATL█SQVH█LDKV█GLLPFLNPEVPDQFYRIWL
SLFLHAGIVHCLVSVVFQMTILRDLEKLAGWHRISIIFILSGITGNLASAIFLPYR**AEVGPAGSQFGLLA
CLFVELFQSWQLLERPWKAFFNLSAIVLFLFICGLLPWIDNIAHIFGFLSGMLLAFAFLPYITF**GTSDKY
RKRALILVSLLVFAGLFASLVLWLYIYPINWPWIEYLT█FPFTSRF█EKYELDQVLH (SEQ ID NO 1)

IRHOM1

MSEARRDSTSSLQRKKPPWLKLDIPAAVPPAAEEPSFLQPLRRQAFLRSVSMPAETARVPSPHHEPRRLVLQRQT
SITQTIRRGTADWFGVSKDSDSTQKWQRKSIRHCSQRYGKLKPQVIRELDLPSQDNVSLTSTETPPPLYVGPCQL
GMQKIIDPLARGRAFRMADDTADGLSAPHTPVTPGAASLCSFSSSRSGFNRLPRRRKRESVAKMSFRAAAALVKG
RSIRDGTLRRGQRRSFTPASFLEEDMVDFPDELDTSFFAREGVLHEEMSTYPDEVFESPSEAALKDWEKAPDQAD
LTGGALDRSELERSHLMLPLERGWRKQKEGGPLAPQPKVRLRQEVVSAAGPRRGQRIAVPVRKLFAREKRPYGLG
MVGRLTNRTYRKRIDSYVKRQIEDMDDHRPFFTYWLTFVHSLVTILAVCIYGIAPVGFSQHETVDSVLRKRGVYE
NVKYVQQENFWIGPSSEALIHLGAKFSP█MRQDPQVHSFILAAREREKHSA█VRNDRSG█VQTSKEE█SSTLAV
WVKWPVHPSAPDLAGNKRQFGSV█HQDPRV█DEPSSEDPHEWPEDITKWPI█TKSSAG███NHPHMD█VITGRP█
█IGTKGR█EITSREY█DFMRGYFHEEATL█SQVH█MDDV█GLLPFLNPEVPDQFYRLWLS**LFLHAGILHCLVSVC
FQMTVLRDLEKLAGWHRIAIIYLLSGITGNLASAIFLPYRAEVGPAGSQFGILACLFVELFQSWQILARPWRAFF
KLLAVVLFLFAFGLLPWIDNFAHISGFVSGLFLSFAFLPYISFGKFDLYRKRCQIIIFQVVFLGLLAGLVVLFYF
Y**PVRCEWCEFLT█IPFTDKF█EKYELDAQLH (SEQ ID NO 2)

Figure 2

Alignment: iR2: top, iR1: bottom

YWLTFVHIIITLLVICTYGIAPVGFAQHVTTQLVLKNRGVYES
YWLTFVHSLVTILAVCIYGIAPVGFSQHETVDSVLRKRGVYEN

VKYIQQENFWIGPSSIDLIHLGAKFSPEIRKDQQIEQLVRRERDIERTSG VQNDRSG IQTLKKD SE
VKYVQQENFWIGPSSEALIHLGAKFSP MRQDPQVHSFILAAREREKHSA VRNDRSG VQTSKEE SS

TLATFVKWQ    GPSDKSDLSQKQPSAVV HQDPRT EEPASSGAHIWPDDITKWPI TEQAQS    GLL
TLAVWVKWPVHPSAPDLAGNKRQFGS--V HQDPRV DEPSSEDPHEWPEDITKWPI TKSSAG    NHP

HID KIKGRP IGTKGS EITTREY EFMHGYFHEDATL SQVH LDKV GLLPFLNPEVPDQFYRIWL
HMD VITGRP IGTKGR EITSREY DFMRGYFHEEATL SQVH MDDV GLLPFLNPEVPDQFYRLWLS

SLFLHAGIVHCLVSVVFQMT  (SEQ ID NO 3)
SLFLHAGILHCLVSVCFQMT  (SEQ ID NO 4)

Figure 3

SEQUENCE LISTING

```
<160> NUMBER OF SEQ ID NOS: 9

<210> SEQ ID NO 1
<211> LENGTH: 827
<212> TYPE: PRT
<213> ORGANISM: Mus musculus

<400> SEQUENCE: 1

Met Ala Ser Ala Asp Lys Asn Gly Ser Asn Leu Pro Ser Val Ser Gly
1               5                   10                  15

Ser Arg Leu Gln Ser Arg Lys Pro Pro Asn Leu Ser Ile Thr Ile Pro
            20                  25                  30

Pro Pro Glu Ser Gln Ala Pro Gly Glu Gln Asp Ser Met Leu Pro Glu
```

```
                   35                  40                  45
Arg Arg Lys Asn Pro Ala Tyr Leu Lys Ser Val Ser Leu Gln Glu Pro
 50                  55                  60
Arg Gly Arg Trp Gln Glu Gly Ala Glu Lys Arg Pro Gly Phe Arg Arg
 65                  70                  75                  80
Gln Ala Ser Leu Ser Gln Ser Ile Arg Lys Ser Thr Ala Gln Trp Phe
                     85                  90                  95
Gly Val Ser Gly Asp Trp Glu Gly Lys Arg Gln Asn Trp His Arg Arg
                    100                 105                 110
Ser Leu His His Cys Ser Val His Tyr Gly Arg Leu Lys Ala Ser Cys
                    115                 120                 125
Gln Arg Glu Leu Glu Leu Pro Ser Gln Glu Val Pro Ser Phe Gln Gly
                    130                 135                 140
Thr Glu Ser Pro Lys Pro Cys Lys Met Pro Lys Ile Val Asp Pro Leu
145                 150                 155                 160
Ala Arg Gly Arg Ala Phe Arg His Pro Asp Glu Val Asp Arg Pro His
                    165                 170                 175
Ala Ala His Pro Pro Leu Thr Pro Gly Val Leu Ser Leu Thr Ser Phe
                    180                 185                 190
Thr Ser Val Arg Ser Gly Tyr Ser His Leu Pro Arg Arg Lys Arg Ile
                    195                 200                 205
Ser Val Ala His Met Ser Phe Gln Ala Ala Ala Leu Leu Lys Gly
210                 215                 220
Arg Ser Val Leu Asp Ala Thr Gly Gln Arg Cys Arg His Val Lys Arg
225                 230                 235                 240
Ser Phe Ala Tyr Pro Ser Phe Leu Glu Glu Asp Ala Val Asp Gly Ala
                    245                 250                 255
Asp Thr Phe Asp Ser Ser Phe Ser Lys Glu Glu Met Ser Ser Met
                    260                 265                 270
Pro Asp Asp Val Phe Glu Ser Pro Pro Leu Ser Ala Ser Tyr Phe Arg
                    275                 280                 285
Gly Val Pro His Ser Ala Ser Pro Val Ser Pro Asp Gly Val His Ile
                    290                 295                 300
Pro Leu Lys Glu Tyr Ser Gly Gly Arg Ala Leu Gly Pro Gly Thr Gln
305                 310                 315                 320
Arg Gly Lys Arg Ile Ala Ser Lys Val Lys His Phe Ala Phe Asp Arg
                    325                 330                 335
Lys Lys Arg His Tyr Gly Leu Gly Val Val Gly Asn Trp Leu Asn Arg
                    340                 345                 350
Ser Tyr Arg Arg Ser Ile Ser Ser Thr Val Gln Arg Gln Leu Glu Ser
                    355                 360                 365
Phe Asp Ser His Arg Pro Tyr Phe Thr Tyr Trp Leu Thr Phe Val His
                    370                 375                 380
Ile Ile Ile Thr Leu Leu Val Ile Cys Thr Tyr Gly Ile Ala Pro Val
385                 390                 395                 400
Gly Phe Ala Gln His Val Thr Thr Gln Leu Val Leu Lys Asn Arg Gly
                    405                 410                 415
Val Tyr Glu Ser Val Lys Tyr Ile Gln Gln Glu Asn Phe Trp Ile Gly
                    420                 425                 430
Pro Ser Ser Ile Asp Leu Ile His Leu Gly Ala Lys Phe Ser Pro Cys
                    435                 440                 445
Ile Arg Lys Asp Gln Gln Ile Glu Gln Leu Val Arg Arg Glu Arg Asp
                    450                 455                 460
```

Ile Glu Arg Thr Ser Gly Cys Cys Val Gln Asn Asp Arg Ser Gly Cys
465                 470                 475                 480

Ile Gln Thr Leu Lys Lys Asp Cys Ser Glu Thr Leu Ala Thr Phe Val
            485                 490                 495

Lys Trp Gln Asn Asp Thr Gly Pro Ser Asp Lys Ser Asp Leu Ser Gln
        500                 505                 510

Lys Gln Pro Ser Ala Val Val Cys His Gln Asp Pro Arg Thr Cys Glu
    515                 520                 525

Glu Pro Ala Ser Ser Gly Ala His Ile Trp Pro Asp Asp Ile Thr Lys
530                 535                 540

Trp Pro Ile Cys Thr Glu Gln Ala Gln Ser Asn His Thr Gly Leu Leu
545                 550                 555                 560

His Ile Asp Cys Lys Ile Lys Gly Arg Pro Cys Cys Ile Gly Thr Lys
                565                 570                 575

Gly Ser Cys Glu Ile Thr Thr Arg Glu Tyr Cys Glu Phe Met His Gly
            580                 585                 590

Tyr Phe His Glu Asp Ala Thr Leu Cys Ser Gln Val His Cys Leu Asp
        595                 600                 605

Lys Val Cys Gly Leu Leu Pro Phe Leu Asn Pro Glu Val Pro Asp Gln
    610                 615                 620

Phe Tyr Arg Ile Trp Leu Ser Leu Phe Leu His Ala Gly Ile Val His
625                 630                 635                 640

Cys Leu Val Ser Val Val Phe Gln Met Thr Ile Leu Arg Asp Leu Glu
                645                 650                 655

Lys Leu Ala Gly Trp His Arg Ile Ser Ile Ile Phe Ile Leu Ser Gly
            660                 665                 670

Ile Thr Gly Asn Leu Ala Ser Ala Ile Phe Leu Pro Tyr Arg Ala Glu
        675                 680                 685

Val Gly Pro Ala Gly Ser Gln Phe Gly Leu Leu Ala Cys Leu Phe Val
    690                 695                 700

Glu Leu Phe Gln Ser Trp Gln Leu Leu Glu Arg Pro Trp Lys Ala Phe
705                 710                 715                 720

Phe Asn Leu Ser Ala Ile Val Leu Phe Leu Phe Ile Cys Gly Leu Leu
                725                 730                 735

Pro Trp Ile Asp Asn Ile Ala His Ile Phe Gly Phe Leu Ser Gly Met
            740                 745                 750

Leu Leu Ala Phe Ala Phe Leu Pro Tyr Ile Thr Phe Gly Thr Ser Asp
        755                 760                 765

Lys Tyr Arg Lys Arg Ala Leu Ile Leu Val Ser Leu Leu Val Phe Ala
    770                 775                 780

Gly Leu Phe Ala Ser Leu Val Leu Trp Leu Tyr Ile Tyr Pro Ile Asn
785                 790                 795                 800

Trp Pro Trp Ile Glu Tyr Leu Thr Cys Phe Pro Phe Thr Ser Arg Phe
                805                 810                 815

Cys Glu Lys Tyr Glu Leu Asp Gln Val Leu His
            820                 825

<210> SEQ ID NO 2
<211> LENGTH: 856
<212> TYPE: PRT
<213> ORGANISM: Mus musculus

<400> SEQUENCE: 2

Met Ser Glu Ala Arg Arg Asp Ser Thr Ser Ser Leu Gln Arg Lys Lys

-continued

```
  1               5                   10                  15
Pro Pro Trp Leu Lys Leu Asp Ile Pro Ala Ala Val Pro Ala Ala
              20                  25                  30
Glu Glu Pro Ser Phe Leu Gln Pro Leu Arg Arg Gln Ala Phe Leu Arg
              35                  40                  45
Ser Val Ser Met Pro Ala Glu Thr Ala Arg Val Pro Ser Pro His His
 50                  55                  60
Glu Pro Arg Arg Leu Val Leu Gln Arg Gln Thr Ser Ile Thr Gln Thr
 65                  70                  75                  80
Ile Arg Arg Gly Thr Ala Asp Trp Phe Gly Val Ser Lys Asp Ser Asp
              85                  90                  95
Ser Thr Gln Lys Trp Gln Arg Lys Ser Ile Arg His Cys Ser Gln Arg
              100                 105                 110
Tyr Gly Lys Leu Lys Pro Gln Val Ile Arg Glu Leu Asp Leu Pro Ser
              115                 120                 125
Gln Asp Asn Val Ser Leu Thr Ser Thr Glu Thr Pro Pro Leu Tyr
              130                 135                 140
Val Gly Pro Cys Gln Leu Gly Met Gln Lys Ile Ile Asp Pro Leu Ala
145                 150                 155                 160
Arg Gly Arg Ala Phe Arg Met Ala Asp Asp Thr Ala Asp Gly Leu Ser
                  165                 170                 175
Ala Pro His Thr Pro Val Thr Pro Gly Ala Ala Ser Leu Cys Ser Phe
                  180                 185                 190
Ser Ser Ser Arg Ser Gly Phe Asn Arg Leu Pro Arg Arg Lys Arg
                  195                 200                 205
Glu Ser Val Ala Lys Met Ser Phe Arg Ala Ala Ala Leu Val Lys
                  210                 215                 220
Gly Arg Ser Ile Arg Asp Gly Thr Leu Arg Arg Gly Gln Arg Arg Ser
225                 230                 235                 240
Phe Thr Pro Ala Ser Phe Leu Glu Glu Asp Met Val Asp Phe Pro Asp
                  245                 250                 255
Glu Leu Asp Thr Ser Phe Phe Ala Arg Glu Gly Val Leu His Glu Glu
                  260                 265                 270
Met Ser Thr Tyr Pro Asp Glu Val Phe Glu Ser Pro Ser Glu Ala Ala
                  275                 280                 285
Leu Lys Asp Trp Glu Lys Ala Pro Asp Gln Ala Asp Leu Thr Gly Gly
                  290                 295                 300
Ala Leu Asp Arg Ser Glu Leu Glu Arg Ser His Leu Met Leu Pro Leu
305                 310                 315                 320
Glu Arg Gly Trp Arg Lys Gln Lys Glu Gly Gly Pro Leu Ala Pro Gln
                  325                 330                 335
Pro Lys Val Arg Leu Arg Gln Glu Val Ser Ala Ala Gly Pro Arg
                  340                 345                 350
Arg Gly Gln Arg Ile Ala Val Pro Val Arg Lys Leu Phe Ala Arg Glu
                  355                 360                 365
Lys Arg Pro Tyr Gly Leu Gly Met Val Gly Arg Leu Thr Asn Arg Thr
                  370                 375                 380
Tyr Arg Lys Arg Ile Asp Ser Tyr Val Lys Arg Gln Ile Glu Asp Met
385                 390                 395                 400
Asp Asp His Arg Pro Phe Phe Thr Tyr Trp Leu Thr Phe Val His Ser
                  405                 410                 415
Leu Val Thr Ile Leu Ala Val Cys Ile Tyr Gly Ile Ala Pro Val Gly
                  420                 425                 430
```

-continued

Phe Ser Gln His Glu Thr Val Asp Ser Val Leu Arg Lys Arg Gly Val
    435                 440                 445

Tyr Glu Asn Val Lys Tyr Val Gln Gln Glu Asn Phe Trp Ile Gly Pro
    450                 455                 460

Ser Ser Glu Ala Leu Ile His Leu Gly Ala Lys Phe Ser Pro Cys Met
465                 470                 475                 480

Arg Gln Asp Pro Gln Val His Ser Phe Ile Leu Ala Ala Arg Glu Arg
                485                 490                 495

Glu Lys His Ser Ala Cys Cys Val Arg Asn Asp Arg Ser Gly Cys Val
            500                 505                 510

Gln Thr Ser Lys Glu Glu Cys Ser Ser Thr Leu Ala Val Trp Val Lys
        515                 520                 525

Trp Pro Val His Pro Ser Ala Pro Asp Leu Ala Gly Asn Lys Arg Gln
    530                 535                 540

Phe Gly Ser Val Cys His Gln Asp Pro Arg Val Cys Asp Glu Pro Ser
545                 550                 555                 560

Ser Glu Asp Pro His Glu Trp Pro Glu Asp Ile Thr Lys Trp Pro Ile
                565                 570                 575

Cys Thr Lys Ser Ser Ala Gly Asn His Thr Asn His Pro His Met Asp
            580                 585                 590

Cys Val Ile Thr Gly Arg Pro Cys Cys Ile Gly Thr Lys Gly Arg Cys
        595                 600                 605

Glu Ile Thr Ser Arg Glu Tyr Cys Asp Phe Met Arg Gly Tyr Phe His
    610                 615                 620

Glu Glu Ala Thr Leu Cys Ser Gln Val His Cys Met Asp Asp Val Cys
625                 630                 635                 640

Gly Leu Leu Pro Phe Leu Asn Pro Glu Val Pro Asp Gln Phe Tyr Arg
                645                 650                 655

Leu Trp Leu Ser Leu Phe Leu His Ala Gly Ile Leu His Cys Leu Val
            660                 665                 670

Ser Val Cys Phe Gln Met Thr Val Leu Arg Asp Leu Glu Lys Leu Ala
        675                 680                 685

Gly Trp His Arg Ile Ala Ile Ile Tyr Leu Leu Ser Gly Ile Thr Gly
    690                 695                 700

Asn Leu Ala Ser Ala Ile Phe Leu Pro Tyr Arg Ala Glu Val Gly Pro
705                 710                 715                 720

Ala Gly Ser Gln Phe Gly Ile Leu Ala Cys Leu Phe Val Glu Leu Phe
                725                 730                 735

Gln Ser Trp Gln Ile Leu Ala Arg Pro Trp Arg Ala Phe Phe Lys Leu
            740                 745                 750

Leu Ala Val Val Leu Phe Leu Phe Ala Phe Gly Leu Leu Pro Trp Ile
        755                 760                 765

Asp Asn Phe Ala His Ile Ser Gly Phe Val Ser Gly Leu Phe Leu Ser
    770                 775                 780

Phe Ala Phe Leu Pro Tyr Ile Ser Phe Gly Lys Phe Asp Leu Tyr Arg
785                 790                 795                 800

Lys Arg Cys Gln Ile Ile Ile Phe Gln Val Val Phe Leu Gly Leu Leu
                805                 810                 815

Ala Gly Leu Val Val Leu Phe Tyr Phe Tyr Pro Val Arg Cys Glu Trp
            820                 825                 830

Cys Glu Phe Leu Thr Cys Ile Pro Phe Thr Asp Lys Phe Cys Glu Lys
        835                 840                 845

Tyr Glu Leu Asp Ala Gln Leu His
        850                 855

<210> SEQ ID NO 3
<211> LENGTH: 273
<212> TYPE: PRT
<213> ORGANISM: Artificial Sequence
<220> FEATURE:
<223> OTHER INFORMATION: Synthetic Peptide

<400> SEQUENCE: 3

Tyr Trp Leu Thr Phe Val His Ile Ile Thr Leu Leu Val Ile Cys
1               5                   10                  15

Thr Tyr Gly Ile Ala Pro Val Gly Phe Ala Gln His Val Thr Thr Gln
            20                  25                  30

Leu Val Leu Lys Asn Arg Gly Val Tyr Glu Ser Val Lys Tyr Ile Gln
        35                  40                  45

Gln Glu Asn Phe Trp Ile Gly Pro Ser Ser Ile Asp Leu Ile His Leu
    50                  55                  60

Gly Ala Lys Phe Ser Pro Cys Ile Arg Lys Asp Gln Gln Ile Glu Gln
65                  70                  75                  80

Leu Val Arg Arg Glu Arg Asp Ile Glu Arg Thr Ser Gly Cys Cys Val
                85                  90                  95

Gln Asn Asp Arg Ser Gly Cys Ile Gln Thr Leu Lys Lys Asp Cys Ser
            100                 105                 110

Glu Thr Leu Ala Thr Phe Val Lys Trp Gln Asn Asp Thr Gly Pro Ser
        115                 120                 125

Asp Lys Ser Asp Leu Ser Gln Lys Gln Pro Ser Ala Val Val Cys His
    130                 135                 140

Gln Asp Pro Arg Thr Cys Glu Glu Pro Ala Ser Ser Gly Ala His Ile
145                 150                 155                 160

Trp Pro Asp Asp Ile Thr Lys Trp Pro Ile Cys Thr Glu Gln Ala Gln
                165                 170                 175

Ser Asn His Thr Gly Leu Leu His Ile Asp Cys Lys Ile Lys Gly Arg
            180                 185                 190

Pro Cys Cys Ile Gly Thr Lys Gly Ser Cys Glu Ile Thr Thr Arg Glu
        195                 200                 205

Tyr Cys Glu Phe Met His Gly Tyr Phe His Glu Asp Ala Thr Leu Cys
    210                 215                 220

Ser Gln Val His Cys Leu Asp Lys Val Cys Gly Leu Leu Pro Phe Leu
225                 230                 235                 240

Asn Pro Glu Val Pro Asp Gln Phe Tyr Arg Ile Trp Leu Ser Leu Phe
                245                 250                 255

Leu His Ala Gly Ile Val His Cys Leu Val Ser Val Val Phe Gln Met
            260                 265                 270

Thr

<210> SEQ ID NO 4
<211> LENGTH: 271
<212> TYPE: PRT
<213> ORGANISM: Artificial Sequence
<220> FEATURE:
<223> OTHER INFORMATION: Synthetic Peptide

<400> SEQUENCE: 4

Tyr Trp Leu Thr Phe Val His Ser Leu Val Thr Ile Leu Ala Val Cys
1               5                   10                  15

```
Ile Tyr Gly Ile Ala Pro Val Gly Phe Ser Gln His Glu Thr Val Asp
             20                  25                  30

Ser Val Leu Arg Lys Arg Gly Val Tyr Glu Asn Val Lys Tyr Val Gln
         35                  40                  45

Gln Glu Asn Phe Trp Ile Gly Pro Ser Ser Glu Ala Leu Ile His Leu
     50                  55                  60

Gly Ala Lys Phe Ser Pro Cys Met Arg Gln Asp Pro Gln Val His Ser
65                  70                  75                  80

Phe Ile Leu Ala Ala Arg Glu Arg Glu Lys His Ser Ala Cys Cys Val
                 85                  90                  95

Arg Asn Asp Arg Ser Gly Cys Val Gln Thr Ser Lys Glu Glu Cys Ser
            100                 105                 110

Ser Thr Leu Ala Val Trp Val Lys Trp Pro Val His Pro Ser Ala Pro
        115                 120                 125

Asp Leu Ala Gly Asn Lys Arg Gln Phe Gly Ser Val Cys His Gln Asp
    130                 135                 140

Pro Arg Val Cys Asp Glu Pro Ser Ser Glu Asp Pro His Glu Trp Pro
145                 150                 155                 160

Glu Asp Ile Thr Lys Trp Pro Ile Cys Thr Lys Ser Ser Ala Gly Asn
                165                 170                 175

His Thr Asn His Pro His Met Asp Cys Val Ile Thr Gly Arg Pro Cys
            180                 185                 190

Cys Ile Gly Thr Lys Gly Arg Cys Glu Ile Thr Ser Arg Glu Tyr Cys
        195                 200                 205

Asp Phe Met Arg Gly Tyr Phe His Glu Glu Ala Thr Leu Cys Ser Gln
    210                 215                 220

Val His Cys Met Asp Asp Val Cys Gly Leu Leu Pro Phe Leu Asn Pro
225                 230                 235                 240

Glu Val Pro Asp Gln Phe Tyr Arg Leu Trp Leu Ser Leu Phe Leu His
                245                 250                 255

Ala Gly Ile Leu His Cys Leu Val Ser Val Cys Phe Gln Met Thr
            260                 265                 270

<210> SEQ ID NO 5
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 5

Ser Ala Pro Asp Leu Ala Gly Asn Lys Arg Gln Phe Gly Ser Val Cys
1               5                   10                  15

His Gln Asp Pro Arg Val Cys Asp Glu Pro Ser Ser Glu Asp Pro His
            20                  25                  30

Glu Trp Pro Glu Asp Ile Thr Lys Trp Pro Ile Cys Thr Lys Ser Ser
        35                  40                  45

Ala Gly
    50

<210> SEQ ID NO 6
<211> LENGTH: 52
<212> TYPE: PRT
<213> ORGANISM: Artificial Sequence
<220> FEATURE:
<223> OTHER INFORMATION: Synthetic Peptide

<400> SEQUENCE: 6
```

```
Gly Pro Ser Asp Lys Ser Asp Leu Ser Gln Lys Gln Pro Ser Ala Val
1               5                   10                  15

Val Cys His Gln Asp Pro Arg Thr Cys Glu Pro Ala Ser Ser Gly
            20                  25                  30

Ala His Ile Trp Pro Asp Asp Ile Thr Lys Trp Pro Ile Cys Thr Glu
            35                  40                  45

Gln Ala Gln Ser
        50

<210> SEQ ID NO 7
<211> LENGTH: 855
<212> TYPE: PRT
<213> ORGANISM: Homo sapiens

<400> SEQUENCE: 7

Met Ser Glu Ala Arg Arg Asp Ser Thr Ser Ser Leu Gln Arg Lys Lys
1               5                   10                  15

Pro Pro Trp Leu Lys Leu Asp Ile Pro Ser Ala Val Pro Leu Thr Ala
            20                  25                  30

Glu Glu Pro Ser Phe Leu Gln Pro Leu Arg Arg Gln Ala Phe Leu Arg
            35                  40                  45

Ser Val Ser Met Pro Ala Glu Thr Ala His Ile Ser Ser Pro His His
    50                  55                  60

Glu Leu Arg Arg Pro Val Leu Gln Arg Gln Thr Ser Ile Thr Gln Thr
65                  70                  75                  80

Ile Arg Arg Gly Thr Ala Asp Trp Phe Gly Val Ser Lys Asp Ser Asp
                85                  90                  95

Ser Thr Gln Lys Trp Gln Arg Lys Ser Ile Arg His Cys Ser Gln Arg
            100                 105                 110

Tyr Gly Lys Leu Lys Pro Gln Val Leu Arg Glu Leu Asp Leu Pro Ser
            115                 120                 125

Gln Asp Asn Val Ser Leu Thr Ser Thr Glu Thr Pro Pro Pro Leu Tyr
    130                 135                 140

Val Gly Pro Cys Gln Leu Gly Met Gln Lys Ile Ile Asp Pro Leu Ala
145                 150                 155                 160

Arg Gly Arg Ala Phe Arg Val Ala Asp Asp Thr Ala Glu Gly Leu Ser
                165                 170                 175

Ala Pro His Thr Pro Val Thr Pro Gly Ala Ala Ser Leu Cys Ser Phe
            180                 185                 190

Ser Ser Ser Arg Ser Gly Phe His Arg Leu Pro Arg Arg Arg Lys Arg
            195                 200                 205

Glu Ser Val Ala Lys Met Ser Phe Arg Ala Ala Ala Leu Met Lys
            210                 215                 220

Gly Arg Ser Val Arg Asp Gly Thr Phe Arg Arg Ala Gln Arg Arg Ser
225                 230                 235                 240

Phe Thr Pro Ala Ser Phe Leu Glu Glu Asp Thr Thr Asp Phe Pro Asp
                245                 250                 255

Glu Leu Asp Thr Ser Phe Phe Ala Arg Glu Gly Ile Leu His Glu Glu
            260                 265                 270

Leu Ser Thr Tyr Pro Asp Glu Val Phe Glu Ser Pro Glu Ala Ala
            275                 280                 285

Leu Lys Asp Trp Glu Lys Ala Pro Glu Gln Ala Asp Leu Thr Gly Gly
    290                 295                 300

Ala Leu Asp Arg Ser Glu Leu Glu Arg Ser His Leu Met Leu Pro Leu
```

```
        305                 310                 315                 320
Glu Arg Gly Trp Arg Lys Gln Lys Glu Gly Ala Ala Ala Pro Gln Pro
                325                 330                 335

Lys Val Arg Leu Arg Gln Glu Val Val Ser Thr Ala Gly Pro Arg Arg
                340                 345                 350

Gly Gln Arg Ile Ala Val Pro Val Arg Lys Leu Phe Ala Arg Glu Lys
                355                 360                 365

Arg Pro Tyr Gly Leu Gly Met Val Gly Arg Leu Thr Asn Arg Thr Tyr
370                 375                 380

Arg Lys Arg Ile Asp Ser Phe Val Lys Arg Gln Ile Glu Asp Met Asp
385                 390                 395                 400

Asp His Arg Pro Phe Phe Thr Tyr Trp Leu Thr Phe Val His Ser Leu
                405                 410                 415

Val Thr Ile Leu Ala Val Cys Ile Tyr Gly Ile Ala Pro Val Gly Phe
                420                 425                 430

Ser Gln His Glu Thr Val Asp Ser Val Leu Arg Asn Arg Gly Val Tyr
                435                 440                 445

Glu Asn Val Lys Tyr Val Gln Gln Glu Asn Phe Trp Ile Gly Pro Ser
450                 455                 460

Ser Glu Ala Leu Ile His Leu Gly Ala Lys Phe Ser Pro Cys Met Arg
465                 470                 475                 480

Gln Asp Pro Gln Val His Ser Phe Ile Arg Ser Ala Arg Glu Arg Glu
                485                 490                 495

Lys His Ser Ala Cys Cys Val Arg Asn Asp Arg Ser Gly Cys Val Gln
                500                 505                 510

Thr Ser Glu Glu Glu Cys Ser Ser Thr Leu Ala Val Trp Val Lys Trp
                515                 520                 525

Pro Ile His Pro Ser Ala Pro Glu Leu Ala Gly His Lys Arg Gln Phe
                530                 535                 540

Gly Ser Val Cys His Gln Asp Pro Arg Val Cys Asp Glu Pro Ser Ser
545                 550                 555                 560

Glu Asp Pro His Glu Trp Pro Glu Asp Ile Thr Lys Trp Pro Ile Cys
                565                 570                 575

Thr Lys Asn Ser Ala Gly Asn His Thr Asn His Pro His Met Asp Cys
                580                 585                 590

Val Ile Thr Gly Arg Pro Cys Cys Ile Gly Thr Lys Gly Arg Cys Glu
                595                 600                 605

Ile Thr Ser Arg Glu Tyr Cys Asp Phe Met Arg Gly Tyr Phe His Glu
                610                 615                 620

Glu Ala Thr Leu Cys Ser Gln Val His Cys Met Asp Asp Val Cys Gly
625                 630                 635                 640

Leu Leu Pro Phe Leu Asn Pro Glu Val Pro Asp Gln Phe Tyr Arg Leu
                645                 650                 655

Trp Leu Ser Leu Phe Leu His Ala Gly Ile Leu His Cys Leu Val Ser
                660                 665                 670

Ile Cys Phe Gln Met Thr Val Leu Arg Asp Leu Glu Lys Leu Ala Gly
                675                 680                 685

Trp His Arg Ile Ala Ile Tyr Leu Leu Ser Gly Val Thr Gly Asn
                690                 695                 700

Leu Ala Ser Ala Ile Phe Leu Pro Tyr Arg Ala Glu Val Gly Pro Ala
705                 710                 715                 720

Gly Ser Gln Phe Gly Ile Leu Ala Cys Leu Phe Val Glu Leu Phe Gln
                725                 730                 735
```

```
Ser Trp Gln Ile Leu Ala Arg Pro Trp Arg Ala Phe Lys Leu Leu
            740                 745                 750

Ala Val Val Leu Phe Leu Phe Thr Phe Gly Leu Leu Pro Trp Ile Asp
            755                 760                 765

Asn Phe Ala His Ile Ser Gly Phe Ile Ser Gly Leu Phe Leu Ser Phe
770                 775                 780

Ala Phe Leu Pro Tyr Ile Ser Phe Gly Lys Phe Asp Leu Tyr Arg Lys
785                 790                 795                 800

Arg Cys Gln Ile Ile Ile Phe Gln Val Val Phe Leu Gly Leu Leu Ala
            805                 810                 815

Gly Leu Val Val Leu Phe Tyr Val Tyr Pro Val Arg Cys Glu Trp Cys
            820                 825                 830

Glu Phe Leu Thr Cys Ile Pro Phe Thr Asp Lys Phe Cys Glu Lys Tyr
            835                 840                 845

Glu Leu Asp Ala Gln Leu His
            850                 855

<210> SEQ ID NO 8
<211> LENGTH: 827
<212> TYPE: PRT
<213> ORGANISM: Homo sapiens

<400> SEQUENCE: 8

Met Ala Ser Ala Asp Lys Asn Gly Gly Ser Val Ser Val Ser Ser
1               5                   10                  15

Ser Arg Leu Gln Ser Arg Lys Pro Pro Asn Leu Ser Ile Thr Ile Pro
            20                  25                  30

Pro Pro Glu Lys Glu Thr Gln Ala Pro Gly Glu Gln Asp Ser Met Leu
            35                  40                  45

Pro Glu Arg Lys Asn Pro Ala Tyr Leu Lys Ser Val Ser Leu Gln Glu
50                  55                  60

Pro Arg Ser Arg Trp Gln Glu Ser Glu Lys Arg Pro Gly Phe Arg
65                  70                  75                  80

Arg Gln Ala Ser Leu Ser Gln Ser Ile Arg Lys Gly Ala Ala Gln Trp
                85                  90                  95

Phe Gly Val Ser Gly Asp Trp Glu Gly Gln Arg Gln Trp Gln Arg
            100                 105                 110

Arg Ser Leu His His Cys Ser Met Arg Tyr Gly Arg Leu Lys Ala Ser
            115                 120                 125

Cys Gln Arg Asp Leu Glu Leu Pro Ser Gln Glu Ala Pro Ser Phe Gln
130                 135                 140

Gly Thr Glu Ser Pro Lys Pro Cys Lys Met Pro Lys Ile Val Asp Pro
145                 150                 155                 160

Leu Ala Arg Gly Arg Ala Phe Arg His Pro Glu Glu Met Asp Arg Pro
                165                 170                 175

His Ala Pro His Pro Leu Thr Pro Gly Val Leu Ser Leu Thr Ser
            180                 185                 190

Phe Thr Ser Val Arg Ser Gly Tyr Ser His Leu Pro Arg Arg Lys Arg
            195                 200                 205

Met Ser Val Ala His Met Ser Leu Gln Ala Ala Ala Leu Leu Lys
            210                 215                 220

Gly Arg Ser Val Leu Asp Ala Thr Gly Gln Arg Cys Arg Val Val Lys
225                 230                 235                 240

Arg Ser Phe Ala Phe Pro Ser Phe Leu Glu Glu Asp Val Val Asp Gly
```

```
            245             250             255
Ala Asp Thr Phe Asp Ser Ser Phe Phe Ser Lys Glu Glu Met Ser Ser
            260             265             270

Met Pro Asp Asp Val Phe Glu Ser Pro Pro Leu Ser Ala Ser Tyr Phe
            275             280             285

Arg Gly Ile Pro His Ser Ala Ser Pro Val Ser Pro Asp Gly Val Gln
            290             295             300

Ile Pro Leu Lys Glu Tyr Gly Arg Ala Pro Val Pro Gly Pro Arg Arg
305             310             315             320

Gly Lys Arg Ile Ala Ser Lys Val Lys His Phe Ala Phe Asp Arg Lys
            325             330             335

Lys Arg His Tyr Gly Leu Gly Val Val Gly Asn Trp Leu Asn Arg Ser
            340             345             350

Tyr Arg Arg Ser Ile Ser Ser Thr Val Gln Arg Gln Leu Glu Ser Phe
            355             360             365

Asp Ser His Arg Pro Tyr Phe Thr Tyr Trp Leu Thr Phe Val His Val
            370             375             380

Ile Ile Thr Leu Leu Val Ile Cys Thr Tyr Gly Ile Ala Pro Val Gly
385             390             395             400

Phe Ala Gln His Val Thr Thr Gln Leu Val Leu Arg Asn Lys Gly Val
            405             410             415

Tyr Glu Ser Val Lys Tyr Ile Gln Gln Glu Asn Phe Trp Val Gly Pro
            420             425             430

Ser Ser Ile Asp Leu Ile His Leu Gly Ala Lys Phe Ser Pro Cys Ile
            435             440             445

Arg Lys Asp Gly Gln Ile Glu Gln Leu Val Leu Arg Glu Arg Asp Leu
450             455             460

Glu Arg Asp Ser Gly Cys Cys Val Gln Asn Asp His Ser Gly Cys Ile
465             470             475             480

Gln Thr Gln Arg Lys Asp Cys Ser Glu Thr Leu Ala Thr Phe Val Lys
            485             490             495

Trp Gln Asp Asp Thr Gly Pro Pro Met Asp Lys Ser Asp Leu Gly Gln
            500             505             510

Lys Arg Thr Ser Gly Ala Val Cys His Gln Asp Pro Arg Thr Cys Glu
            515             520             525

Glu Pro Ala Ser Ser Gly Ala His Ile Trp Pro Asp Asp Ile Thr Lys
            530             535             540

Trp Pro Ile Cys Thr Glu Gln Ala Arg Ser Asn His Thr Gly Phe Leu
545             550             555             560

His Met Asp Cys Glu Ile Lys Gly Arg Pro Cys Cys Ile Gly Thr Lys
            565             570             575

Gly Ser Cys Glu Ile Thr Thr Arg Glu Tyr Cys Glu Phe Met His Gly
            580             585             590

Tyr Phe His Glu Glu Ala Thr Leu Cys Ser Gln Val His Cys Leu Asp
            595             600             605

Lys Val Cys Gly Leu Leu Pro Phe Leu Asn Pro Glu Val Pro Asp Gln
            610             615             620

Phe Tyr Arg Leu Trp Leu Ser Leu Phe Leu His Ala Gly Val Val His
625             630             635             640

Cys Leu Val Ser Val Val Phe Gln Met Thr Ile Leu Arg Asp Leu Glu
            645             650             655

Lys Leu Ala Gly Trp His Arg Ile Ala Ile Ile Phe Ile Leu Ser Gly
            660             665             670
```

Ile Thr Gly Asn Leu Ala Ser Ala Ile Phe Leu Pro Tyr Arg Ala Glu
            675                 680                 685

Val Gly Pro Ala Gly Ser Gln Phe Gly Leu Leu Ala Cys Leu Phe Val
690                 695                 700

Glu Leu Phe Gln Ser Trp Pro Leu Leu Glu Arg Pro Trp Lys Ala Phe
705                 710                 715                 720

Leu Asn Leu Ser Ala Ile Val Leu Phe Leu Phe Ile Cys Gly Leu Leu
                725                 730                 735

Pro Trp Ile Asp Asn Ile Ala His Ile Phe Gly Phe Leu Ser Gly Leu
                740                 745                 750

Leu Leu Ala Phe Ala Phe Leu Pro Tyr Ile Thr Phe Gly Thr Ser Asp
            755                 760                 765

Lys Tyr Arg Lys Arg Ala Leu Ile Leu Val Ser Leu Leu Ala Phe Ala
            770                 775                 780

Gly Leu Phe Ala Ala Leu Val Leu Trp Leu Tyr Ile Tyr Pro Ile Asn
785                 790                 795                 800

Trp Pro Trp Ile Glu His Leu Thr Cys Phe Pro Phe Thr Ser Arg Phe
                805                 810                 815

Cys Glu Lys Tyr Glu Leu Asp Gln Val Leu His
            820                 825

<210> SEQ ID NO 9
<211> LENGTH: 856
<212> TYPE: PRT
<213> ORGANISM: Homo sapiens

<400> SEQUENCE: 9

Met Ala Ser Ala Asp Lys Asn Gly Gly Ser Val Ser Ser Val Ser Ser
1               5                   10                  15

Ser Arg Leu Gln Ser Arg Lys Pro Pro Asn Leu Ser Ile Thr Ile Pro
                20                  25                  30

Pro Pro Glu Lys Glu Thr Gln Ala Pro Gly Glu Gln Asp Ser Met Leu
            35                  40                  45

Pro Glu Gly Phe Gln Asn Arg Arg Leu Lys Lys Ser Gln Pro Arg Thr
50                  55                  60

Trp Ala Ala His Thr Thr Ala Cys Pro Pro Ser Phe Leu Pro Lys Arg
65                  70                  75                  80

Lys Asn Pro Ala Tyr Leu Lys Ser Val Ser Leu Gln Glu Pro Arg Ser
                85                  90                  95

Arg Trp Gln Glu Ser Ser Glu Lys Arg Pro Gly Phe Arg Gln Ala
            100                 105                 110

Ser Leu Ser Gln Ser Ile Arg Lys Gly Ala Ala Gln Trp Phe Gly Val
            115                 120                 125

Ser Gly Asp Trp Glu Gly Gln Arg Gln Trp Gln Arg Ser Leu
130                 135                 140

His His Cys Ser Met Arg Tyr Gly Arg Leu Lys Ala Ser Cys Gln Arg
145                 150                 155                 160

Asp Leu Glu Leu Pro Ser Gln Glu Ala Pro Ser Phe Gln Gly Thr Glu
                165                 170                 175

Ser Pro Lys Pro Cys Lys Met Pro Lys Ile Val Asp Pro Leu Ala Arg
            180                 185                 190

Gly Arg Ala Phe Arg His Pro Glu Glu Met Asp Arg Pro His Ala Pro
            195                 200                 205

His Pro Pro Leu Thr Pro Gly Val Leu Ser Leu Thr Ser Phe Thr Ser

```
              210                 215                 220
Val Arg Ser Gly Tyr Ser His Leu Pro Arg Arg Lys Arg Met Ser Val
225                 230                 235                 240

Ala His Met Ser Leu Gln Ala Ala Ala Leu Leu Lys Gly Arg Ser
                245                 250                 255

Val Leu Asp Ala Thr Gly Gln Arg Cys Arg Val Lys Arg Ser Phe
                260                 265                 270

Ala Phe Pro Ser Phe Leu Glu Glu Asp Val Val Asp Gly Ala Asp Thr
                275                 280                 285

Phe Asp Ser Ser Phe Phe Ser Lys Glu Glu Met Ser Ser Met Pro Asp
                290                 295                 300

Asp Val Phe Glu Ser Pro Pro Leu Ser Ala Ser Tyr Phe Arg Gly Ile
305                 310                 315                 320

Pro His Ser Ala Ser Pro Val Ser Pro Asp Gly Val Gln Ile Pro Leu
                325                 330                 335

Lys Glu Tyr Gly Arg Ala Pro Val Pro Gly Pro Arg Arg Gly Lys Arg
                340                 345                 350

Ile Ala Ser Lys Val Lys His Phe Ala Phe Asp Arg Lys Lys Arg His
                355                 360                 365

Tyr Gly Leu Gly Val Val Gly Asn Trp Leu Asn Arg Ser Tyr Arg Arg
                370                 375                 380

Ser Ile Ser Ser Thr Val Gln Arg Gln Leu Glu Ser Phe Asp Ser His
385                 390                 395                 400

Arg Pro Tyr Phe Thr Tyr Trp Leu Thr Phe Val His Val Ile Ile Thr
                405                 410                 415

Leu Leu Val Ile Cys Thr Tyr Gly Ile Ala Pro Val Gly Phe Ala Gln
                420                 425                 430

His Val Thr Thr Gln Leu Val Leu Arg Asn Lys Gly Val Tyr Glu Ser
                435                 440                 445

Val Lys Tyr Ile Gln Gln Glu Asn Phe Trp Val Gly Pro Ser Ser Ile
                450                 455                 460

Asp Leu Ile His Leu Gly Ala Lys Phe Ser Pro Cys Ile Arg Lys Asp
465                 470                 475                 480

Gly Gln Ile Glu Gln Leu Val Leu Arg Glu Arg Asp Leu Glu Arg Asp
                485                 490                 495

Ser Gly Cys Cys Val Gln Asn Asp His Ser Gly Cys Ile Gln Thr Gln
                500                 505                 510

Arg Lys Asp Cys Ser Glu Thr Leu Ala Thr Phe Val Lys Trp Gln Asp
                515                 520                 525

Asp Thr Gly Pro Pro Met Asp Lys Ser Asp Leu Gly Gln Lys Arg Thr
530                 535                 540

Ser Gly Ala Val Cys His Gln Asp Pro Arg Thr Cys Glu Glu Pro Ala
545                 550                 555                 560

Ser Ser Gly Ala His Ile Trp Pro Asp Asp Ile Thr Lys Trp Pro Ile
                565                 570                 575

Cys Thr Glu Gln Ala Arg Ser Asn His Thr Gly Phe Leu His Met Asp
                580                 585                 590

Cys Glu Ile Lys Gly Arg Pro Cys Cys Ile Gly Thr Lys Gly Ser Cys
                595                 600                 605

Glu Ile Thr Thr Arg Glu Tyr Cys Glu Phe Met His Gly Tyr Phe His
                610                 615                 620

Glu Glu Ala Thr Leu Cys Ser Gln Val His Cys Leu Asp Lys Val Cys
625                 630                 635                 640
```

```
Gly Leu Leu Pro Phe Leu Asn Pro Glu Val Pro Asp Gln Phe Tyr Arg
                645                 650                 655

Leu Trp Leu Ser Leu Phe Leu His Ala Gly Val Val His Cys Leu Val
                660                 665                 670

Ser Val Val Phe Gln Met Thr Ile Leu Arg Asp Leu Glu Lys Leu Ala
                675                 680                 685

Gly Trp His Arg Ile Ala Ile Ile Phe Ile Leu Ser Gly Ile Thr Gly
        690                 695                 700

Asn Leu Ala Ser Ala Ile Phe Leu Pro Tyr Arg Ala Glu Val Gly Pro
705                 710                 715                 720

Ala Gly Ser Gln Phe Gly Leu Leu Ala Cys Leu Phe Val Glu Leu Phe
                725                 730                 735

Gln Ser Trp Pro Leu Leu Glu Arg Pro Trp Lys Ala Phe Leu Asn Leu
                740                 745                 750

Ser Ala Ile Val Leu Phe Leu Phe Ile Cys Gly Leu Leu Pro Trp Ile
                755                 760                 765

Asp Asn Ile Ala His Ile Phe Gly Phe Leu Ser Gly Leu Leu Leu Ala
        770                 775                 780

Phe Ala Phe Leu Pro Tyr Ile Thr Phe Gly Thr Ser Asp Lys Tyr Arg
785                 790                 795                 800

Lys Arg Ala Leu Ile Leu Val Ser Leu Leu Ala Phe Ala Gly Leu Phe
                805                 810                 815

Ala Ala Leu Val Leu Trp Leu Tyr Ile Tyr Pro Ile Asn Trp Pro Trp
                820                 825                 830

Ile Glu His Leu Thr Cys Phe Pro Phe Thr Ser Arg Phe Cys Glu Lys
        835                 840                 845

Tyr Glu Leu Asp Gln Val Leu His
850                 855
```

IDENTIFICATION OF AN INHIBITOR OF IRHOM1 OR AN INHIBITOR OF IRHOM2

RELATED APPLICATIONS

This application is a 35 U.S.C. § 371 national stage filing of International Application No. PCT/US2013/076954, filed on Dec. 20, 2013, which claims the benefit of U.S. Provisional Application No. 61/740,226, filed on Dec. 20, 2012. The entire contents of each of the foregoing applications are hereby incorporated by reference in their entirety.

GOVERNMENT SUPPORT

The research reported herein was supported in part by grant number NIH R01 GM64750. The Government has certain rights in the invention.

BACKGROUND

EGFR (epidermal growth factor receptor) exists on the cell surface and is activated by binding of its specific ligands, including epidermal growth factor and transforming growth factor α (TGFα). Upon activation by its growth factor ligands, EGFR undergoes a transition from an inactive monomeric form to an active homodimer (Yosef Yarden and Joseph Schlessinger (1987), "Epidermal Growth-Factor Induces Rapid, Reversible Aggregation of the Purified Epidermal Growth-Factor Receptor", *Biochemistry* 26 (5): 1443-1451). EGFR dimerization elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation (Oda K, Matsuoka Y, Funahashi A, Kitano H (2005), "A comprehensive pathway map of epidermal growth factor receptor signaling". *Mol. Syst. Biol.* 1 (1): 2005.0010). Such proteins modulate phenotypes such as cell migration, adhesion, and proliferation.

Mutations that lead to EGFR overexpression (known as upregulation) or overactivity have been associated with a number of cancers, including lung cancer, anal cancers (Walker F, Abramowitz L, Benabderrahmane D, Duval X, Descatoire V, Hénin D, Lehy T, Aparicio T (November 2009), "Growth factor receptor expression in anal squamous lesions: modifications associated with oncogenic human papillomavirus and human immunodeficiency virus", *Hum. Pathol.* 40 (11): 1517-27) and glioblastoma multiforme. In this latter case a more or less specific mutation of EGFR, called EGFRvIII is often observed (Kuan C T, Wikstrand C J, Bigner D D (June 2001), (EGF mutant receptor vIII as a molecular target in cancer therapy", *Endocr. Relat. Cancer* 8 (2): 83-96). Mutations, amplifications or misregulations of EGFR or family members are implicated in about 30% of all epithelial cancers. Mutations involving EGFR could lead to its constant activation, which could result in uncontrolled cell division. Consequently, mutations of EGFR have been identified in several types of cancer, and it is the target of an expanding class of anticancer therapies (Zhang H, Berezov A, Wang Q, Zhang G, Drebin J, Murali R, Greene M I (August 2007). "ErbB receptors: from oncogenes to targeted cancer therapies". *J. Clin. Invest.* 117 (8): 2051-8).

The identification of EGFR as an oncogene has led to the development of anticancer therapeutics directed against EGFR, including gefitinib and erlotinib for lung cancer, and cetuximab for colon cancer. Cetuximab and panitumumab are examples of monoclonal antibody inhibitors. Other monoclonals in clinical development are zalutumumab, nimotuzumab, and matuzumab. Another method is using small molecules to inhibit the EGFR tyrosine kinase, which is on the cytoplasmic side of the receptor. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors.

The membrane-anchored metalloproteinase TNFα convertase, TACE (also referred to as "ADAM17") regulates the release of TNFα and EGFR-ligands from cells. As such, inhibiting TACE activity is another pathway by which EGFR activation can be blocked and represents a means of treating EGFR dependent pathologies.

SUMMARY OF THE INVENTION

It has now been found that iRhom1 and the related iRhom2 together support TACE (also referred to as ADAM17) maturation and shedding of the EGFR ligand TGFα. TACE is essential for activating EGFR by releasing TGFα. Based on these results, methods of treating a subject with an EGFR dependent pathology are disclosed herein.

One embodiment of the invention a method for treating a subject with an EGFR dependent pathology. The method comprises the step of administering to the subject an effective amount of an agent ("First Agent") that decreases the biological activity of iRhom1 and an effective amount of an agent ("Second Agent") that decreases the biological activity of iRhom2.

Another embodiment of the invention is method for treating a subject with an EGFR dependent pathology, comprising the step of administering to the subject an effective amount of an agent ("First Agent") that modulates (increases or decreases) formation of a complex between iRhom 1 and TACE and an effective amount of an agent ("Second Agent") that modulates (increases or decreases) formation of a complex between TACE and iRhom2.

Another embodiment of the invention is a method of identifying an agent which can be used in combination with an inhibitor of a biological activity of iRhom2 for the treatment of an EGFR dependent pathology. The method comprises the steps of
  a) combining TACE, iRhom 1 and a test agent under conditions suitable for forming a complex between TACE and iRhom1; and
  b) assessing the quantity of complex formation between TACE and iRhom1. A diminished or increased complex formation between TACE and iRhom1 in the presence of the test agent than in the absence is indicative that the test agent is useful for the treatment of an EGFR dependent pathology in combination with an inhibitor of a biological activity of iRhom2.

Another embodiment of the invention is a method of identifying an agent which can be used in combination with an inhibitor of a biological activity of or iRhom1 for the treatment of an EGFR dependent pathology. The method comprises the steps of
  a) combining TACE, iRhom2 and a test agent under conditions suitable for forming a complex between TACE and iRhom2; and
  b) assessing the quantity of complex formation between TACE and iRhom2. A diminished or increased complex formation between TACE and iRhom2 in the presence of the test agent than in the absence is indicative that the test agent is useful for the treatment of an EGFR dependent pathology in combination with an inhibitor of a biological activity of iRhom1.

Yet another embodiment of the invention is a method of identifying an agent which can be used in combination with an inhibitor of a biological activity of iRhom2 for the treatment of an EGFR dependent pathology. The method comprises the following steps:
a) combining a test agent and a cell which releases an EGFR ligand under conditions suitable for stimulating release of the EGFR ligand, wherein the cell is iRhom2−/− (or iRhom1−/−) or wherein an inhibitor of a biological activity of iRhom2 is additionally combined with the cell and test agent; and
b) assessing the quantity of EGFR ligand, wherein diminished EGFR ligand release in the presence of the test agent than in the absence is indicative that the test agent is useful in combination with an inhibitor of a biological activity of iRhom2 for the treatment of an EGFR dependent pathology.

Another embodiment of the invention is a method of identifying an agent which can be used in combination with an inhibitor of a biological activity of iRhom1 for the treatment of an EGFR dependent pathology. The method comprises the following steps:
a) combining a test agent and a cell which releases an EGFR ligand under conditions suitable for stimulating release of the EGFR ligand, wherein the cell is iRhom1−/− or wherein an inhibitor of a biological activity of iRhom1 is additionally combined with the cell and test agent; and
b) assessing the quantity of EGFR ligand, wherein diminished EGFR ligand release in the presence of the test agent than in the absence is indicative that the test agent is useful in combination with an inhibitor of a biological activity of iRhom1 for the treatment of an EGFR dependent pathology.

Yet another embodiment of the invention is a method of identifying an agent which can be used in combination with an inhibitor of a biological activity of iRhom2 for the treatment of an EGFR dependent pathology. The method comprises the following steps:
a) combining a test agent and a cell which expresses the mature 100 kD form of TACE under conditions suitable for expression of the mature 100 kD form of TACE (e.g., on reducing SDS-PAGE), wherein the cell is either iRhom2−/− or an inhibitor of a biological activity of iRhom2 is additionally combined with the cell and test agent; and
b) assessing the quantity of the mature 100 kD form of TACE that is formed (e.g., on reducing SDS-PAGE), wherein diminished formation of the mature 100 kD form of TACE in the presence of the test agent than in the absence is indicative that the test agent is useful in combination with an inhibitor of a biological activity of iRhom2 for the treatment of an EGFR dependent pathology.

Yet another embodiment of the invention is a method of identifying an agent which can be used in combination with an inhibitor of a biological activity of iRhom1 for the treatment of an EGFR dependent pathology. The method comprises the following steps:
a) combining a test agent and a cell which expresses the mature 100 kD form of TACE (e.g., on reducing SDS-PAGE) under conditions suitable for expressing the mature form of TACE, wherein the cell is either iRhom1−/− or an inhibitor of a biological activity of iRhom1 is additionally combined with the cell and test agent; and
b) assessing the quantity of the mature 100 kD form of TACE that is formed (e.g., on reducing SDS-PAGE), wherein diminished formation of the mature 100 kD form of TACE in the presence of the test agent than in the absence is indicative that the test agent is useful in combination with an inhibitor of a biological activity of iRhom1 for the treatment of an EGFR dependent pathology.

BRIEF DESCRIPTION OF THE FIGURES

FIG. 1. iRhom2 controls TACE maturation in immune cells, but not somatic tissues. (A) Western blots of TACE in tissues and cells from iRhom2−/− (iR2−/−) and littermate controls (WT). In iRhom2−/− mice, mature TACE is absent in bone marrow (BM), strongly reduced in lymph nodes (LN), but present in brain, heart, kidney, liver lung and spleen (differences in mature TACE migration caused by N-linked carbohydrate modifications, blots are representative of 5). (B,C) qPCR (B, n=2) and Western blots (C, n=3) of iRhom1 in mEFs, primary macrophages (MDs) and primary keratinocytes (KCs, iRhom2−/− vs. controls, mean±SD in B, siR1-treated WT mEFs included in C, iRhom1 runs as a doublet in KCs). (D) Representative TACE Western blot of mEFs from WT, iRhom2−/− or Tace−/− animals, n=3. (E) Shedding of TGFα from WT, iRhom2−/−, siR1-treated iRhom2−/−, or Tace−/− mEFs, n=4, mean±SD, *p<0.05. (F) TACE Western blot shows reduction of mature TACE only in siR1-treated iRhom2−/− mEFs, but not in siR1-treated WT controls. (G) qPCR confirmed reduction of iRhom1 in siR1-treated WT or iRhom2−/− mEFs (representative of 3 experiments). (H, I) Western blot of TACE (H) and release of endogenous TGFα (I) from primary keratinocytes from iRhom2−/− or WT mice, n=2, mean±SD. ADAM9, ADAM15 or ERK used as loading control, as indicated.

FIG. 2 shows the amino acid sequence of iRohm2 (SEQ ID NO 1) and iRhom1 (SEQ ID NO 2), respectively.

FIG. 3 shows the alignment of iRohm2 (top) relative to iRhom1. The sequences shown include the extracellular loop, with the most conserved sequences indicated by underlining; bold underlined sequences are the transmembrane domains that "anchor" the extracellular loop domains; shaded cysteine residues are conserved cysteine residues; and other shaded residues indicate glycosylation sites.

DETAILED DESCRIPTION iRhom2 controls the maturation of TACE, yet iRhom2−/− mice are healthy (Adrain, C., Zettl, M., Christova, Y., Taylor, N., and Freeman, M. 2012. Tumor necrosis factor signaling requires iRhom2 to promote trafficking and activation of TACE. *Science* 335:225-228. McIlwain, D. R., Lang, P. A., Maretzky, T., Hamada, K., Ohishi, K., Maney, S. K., Berger, T., Murthy, A., Duncan, G., Xu, H. C., et al. 2012. iRhom2 regulation of TACE controls TNF-mediated protection against *Listeria* and responses to LPS. *Science* 335:229-232. Siggs, O. M., Xiao, N., Wang, Y., Shi, H., Tomisato, W., Li, X., Xia, Y., and Beutler, B. 2012. iRhom2 is required for the secretion of mouse TNFα. Blood 119:5769-5771), whereas Tace−/− mice die perinatally (Horiuchi, K., Kimura, T., Miyamoto, T., Takaishi, H., Okada, Y., Toyama, Y., and Blobel, C. P. 2007. Cutting Edge: TNF-{a}-Converting Enzyme (TACE/ADAM17) Inactivation in Mouse Myeloid Cells Prevents Lethality from Endotoxin Shock. J Immunol 179:2686-2689. Peschon, J. J., Slack, J. L., Reddy, P., Stocking, K. L., Sunnarborg, S. W., Lee, D. C., Russel, W. E., Castner, B. J., Johnson, R. S., Fitzner, J. N., et al. 1998. An essential role for ectodomain shedding in mammalian development. *Science* 282:1281-1284.). To address this apparent paradox, we assessed whether iRhom2 affects TACE maturation in tissues other than macrophages. In Western blots of iRhom2−/− tissues, mature TACE was not detected in bone marrow (BM), was strongly reduced in lymph nodes (LN), but was clearly present in the brain, heart, kidney, liver, lung and spleen (FIG. 1A), in approximate concordance with the expression of the related iRhom1 (BioGPS atlas, mu-iRhom1). We therefore tested whether it is iRhom1 that supports TACE maturation in iRhom2−/− mouse embryonic fibroblasts (mEFs), which express higher iRhom1 levels than macrophages (MΦs, FIG. 1B,C) and have normal levels of mature TACE in Western blots (FIG. 1D, control: Tace−/− mEFs). iRhom2−/− mEFs shed the TACE substrate and EGFR-ligand, TGFα, at comparable levels to wild-type (WT) controls (FIG. 1E). However, in iRhom2−/− mEFs treated with iRhom1 siRNA (siR1), TGFα shedding was strongly reduced (FIG. 1E, control: Tace−/− mEFs). Western blots showed normal mature TACE levels in siR1-treated WT mEFs, but strongly reduced mature TACE in siR1-treated iRhom2−/− mEFs (FIG. 1F, siR1 was effective in both WT and mutant cells, FIG. 1G). Since iRhom1 is not upregulated in iRhom2−/− mEFs (FIG. 1B,C), iRhom1 is sufficient for TACE maturation and function. In iRhom2−/− primary keratinocytes (KC), which expressed similar iRhom1 levels as mEFs (FIG. 1B,C), mature TACE levels and the release of endogenous TGF-α were comparable to controls (FIG. 1H,I). In summary, our results explain why iRhom2−/− mice display no obvious spontaneous pathologies: mature TACE is produced in most somatic tissues of iRhom2−/− mice. The related iRhom1, which is expressed in somatic tissues but not in most hematopoietic cells, appears to support TACE maturation and function in the absence of iRhom2, as shown in fibroblasts.

An "EGFR dependent pathology" is a disease or condition caused by aberrant expression (over expression or under expression) of EGFR or aberrant activity (overactivity or underactivity) of EGFR. Typically, the EGFR dependent pathology is an EGFR dependent cancer, typically a cancer which expresses (or overexpresses) EGFR. Methods of determining whether a cancer expresses or overexpresses EGFR are well known in the art and include a diagnostic immunohistochemistry assay (EGFR pharmDx) which can be used to detect EGFR expression in the tumor material. Exemplary EGFR dependent cancers (also referred to herein as "EGFR expressing cancers") include colorectal cancer, squamous cell carcinoma of the head and neck, lung cancer, anal cancer and glioblastoma multiforme. Treatment according to the disclosed invention is particularly advantageous when the cancer (e.g., the colorectal cancer) is KRAS wild-type. KRAS mutational analysis is commercially available from a number of laboratories. Alternatively, THE EGFR expressing cancer is EGFR wild-type, or EGFR and KRAS wild-type.

Various proteins are described herein by reference to their GenBank Accession Numbers for their human proteins and coding sequences. However, the proteins are not limited to human-derived proteins having the amino acid sequences represented by the disclosed GenBank Accession numbers, but may have an amino acid sequence derived from other animals, particularly, a warm-blooded animal (e.g., rat, guinea pig, mouse, chicken, rabbit, pig, sheep, cow, monkey, etc.).

The term "iRhom1", "Rhbdf1" or rhomboid 5 homolog 1 (*Drosophila*) refer to a protein having an amino acid sequence substantially identical to any of the representative iRhom1 sequences of GenBank Accession Nos. NP_071895.3 (human), AAH23469.1 or NP_034247.2 (mouse) or to the sequence shown in FIG. 2. The human sequence of iRhom1 with GenBank Accession No. NP_071895.3 is shown below:

```
                                                              (SEQ ID NO: 7)
  1   msearrdsts slqrkkppwl kldipsavpl taeepsflqp lrrqaflrsv smpaetahis 61   sphhelrrpv lqrqtsitqt irrgtadwfg vskdsdstqk wqrksirhcs qrygklkpqv 121   lreldlpsqd nvsltstetp pplyvgpcql gmqkiidpla rgrafrvadd taeglsapht 181   pvtpgaaslc sfsssrsgfh rlprrrkres vakmsfraaa almkgrsvrd gtfrraqrrs 241   ftpasfleed ttdfpdeldt sffaregilh eelstypdev fespseaalk dwekapeqad 301   ltggaldrse lershlmlpl ergwrkqkeg aaapqpkvrl rqevvstagp rrgqriavpv 361   rklfarekrp yglgmvgrlt nrtyrkrids fvkrqiedmd dhrpfftywl tfvhslvtil 421   avciygiapv gfsqhetvds vlrnrgvyen vkyvqqenfw igpssealih lgakfspcmr 481   qdpqvhsfir sarerekhsa ccvrndrsgc vqtseeecss tlavwvkwpi hpsapelagh 541   krqfgsvchq dprvcdepss edphewpedi tkwpictkns agnhtnhphm dcvitgrpcc 601   igtkgrceit sreycdfmrg yfheeatlcs qvhcmddvcg llpflnpevp dqfyrlwlsl 661   flhagilhcl vsicfqmtvl rdleklagwh riaiiyllsg vtgnlasaif lpyraevgpa 721   gsqfgilacl fvelfqswqi larpwraffk llavvlflft fgllpwidnf ahisgfisgl 781   flsfaflpyi sfgkfdlyrk rcqiiifqvv flgllaglvv lfyvypvrce wcefltcipf 841   tdkfcekyel daqlh
```

The term "iRhom2", "Rhbdf2", or "rhomboid 5 homolog 2 (Drosophila)" refers to a protein having an amino acid sequence substantially identical to any of the representative iRhom2 sequences of GenBank Accession Nos. NP_001005498.2 or NP_078875.4 (human), NP_001161152.1 (mouse) and NP_001100537.1 (rat) or to the sequence shown in FIG. 2. Suitable cDNA encoding iRhom2 are provided at GenBank Accession Nos. NM_001005498.3 or NM_024599.5 (human), BC052182.1 (mouse) and NM_001107067.1 (rat). The human sequences of iRhom2 with GenBank Accession Nos. NP_001005498.2, NP_078875.4 are shown below:

a protein having an amino acid sequence represented by GenBank Accession No. GenBank Accession Nos. NP_071895.3 (human), AAH23469.1 or NP_034247.2 (mouse) or to the sequence shown in FIG. 2. Decreasing the biological activity, in one embodiment, refers to decreasing the expression of the iRhom1 mRNA or protein. Measurement of transcriptional activity can be performed using any known method, such as immunohistochemistry, reporter assay or RT-PCR, which can also be used to determine whether the biological activity of iRhom1 is decreased. In another embodiment, decreasing the biological activity refers to inhibiting or reducing maturation of TACE. TACE maturation can be detected and quantified by Western blot-

```
                                                            (SEQ ID NO: 8)
  1  masadknggs vssvsssrlq srkppnlsit ipppeketqa pgeqdsmlpe rknpaylksv
 61  slqeprsrwq essekrpgfr rqaslsqsir kgaaqwfgvs gdwegqrqqw qrrslhhcsm
121  rygrlkascq rdlelpsqea psfqgtespk pckmpkivdp largrafrhp eemdrphaph
181  ppltpgvlsl tsftsvrsgy shlprrkrms vahmslqaaa allkgrsvld atgqrcrvvk
241  rsfafpsfle edvvdgadtf dssffskeem ssmpddvfes pplsasyfrg iphsaspvsp
301  dgvqiplkey grapvpgprr gkriaskvkh fafdrkkrhy glgvvgnwln rsyrrsisst
361  vqrqlesfds hrpyftywlt fvhviitllv ictygiapvg faqhvttqlv lrnkgvyesv
421  kyiqqenfwv gpssidlihl gakfspcirk dgqieqlvlr erdlerdsgc cvqndhsgci
481  qtqrkdcset latfvkwqdd tgppmdksdl gqkrtsgavc hqdprtceep assgahiwpd
541  ditkwpicte qarsnhtgfl hmdceikgrp ccigtkgsce ittreycefm hgyfheeatl
601  csqvhcldkv cgllpflnpe vpdqfyrlwl slflhagvvh clvsvvfqmt ilrdleklag
661  whriaiifil sgitgnlasa iflpyraevg pagsqfglla clfvelfqsw pllerpwkaf
721  lnlsaivlfl ficgllpwid niahifgfls glllafaflp yitfgtsdky rkralilvsl
781  lafaglfaal vlwlyiypin wpwiehltcf pftsrfceky eldqvlh (SEQ ID NO: 9)
  1  masadknggs vssysssrlq srkppnlsit ipppeketqa pgeqdsmlpe gfqnrrlkks
 61  qprtwaahtt acppsflpkr knpaylksys lqeprsrwqe ssekrpgfrr qaslsqsirk
121  gaaqwfgvsg dwegqrqqwq rrslhhcsmr ygrlkascqr dlelpsqeap sfqgtespkp
181  ckmpkivdpl argrafrhpe emdrphaphp pltpgvlslt sftsvrsgys hlprrkrmsv
241  ahmslqaaaa llkgrsvlda tgqrcrvvkr sfafpsflee dvvdgadtfd ssffskeems
301  smpddvfesp plsasyfrgi phsaspvspd gvqiplkeyg rapvpgprrg kriaskvkhf
361  afdrkkrhyg lgvvgnwlnr syrrsisstv qrqlesfdsh rpyftywltf vhviitllvi
421  ctygiapvgf aqhvttqlvl rnkgvyesvk yiqqenfwvg pssidlihlg akfspcirkd
481  gqieqlvlre rdlerdsgcc vqndhsgciq tqrkdcsetl atfvkwqddt gppmdksdlg
541  qkrtsgavch qdprtceepa ssgahiwpdd itkwpicteq arsnhtgflh mdceikgrpc
601  cigtkgscei ttreycefmh gyfheeatlc sqvhcldkvc gllpflnpev pdqfyrlwls
661  lflhagvvhc lvsvvfqmti lrdleklagw hriaiifils gitgnlasai flpyraevgp
721  agsqfgllac lfvelfqswp llerpwkafl nlsaivlflf icgllpwidn iahifgflsg
781  lllafaflpy itfgtsdkyr kralilvsll afaglfaalv lwlyiypinw pwiehltcfp
841  ftsrfcekye ldqvlh
```

The term "biological activity of iRhom1" refers to any biological activity associated with the full-length native iRhom1 protein, including the biological activity resulting from its association with TACE. In suitable embodiments, the iRhom1 biological activity is equivalent to the activity of ting. The iRhom1 referred to herein can be a mammalian iRhom1 or in a particular aspect, a human iRhom1 or a splice variant thereof.

The term "biological activity of iRhom2" refers to any biological activity associated with the full length native iRhom2 protein, including the biological activity resulting from its association with TACE. In suitable embodiments, the iRhom2 biological activity is equivalent to the activity of a protein having an amino acid sequence represented by GenBank Accession No. NP_001005498.2, NP_078875.4, NP_001161152.1, or NP_001100537.1 or the amino acid sequence shown in FIG. 2. Decreasing the biological activity, in one embodiment, refers to decreasing the expression of the iRhom2 mRNA or protein. Measurement of transcriptional activity can be performed using any known method, such as immunohistochemistry, reporter assay or RT-PCR, which can also be used to determine whether the biological activity of iRhom2 is decreased. In another embodiment, decreasing the biological activity refers to inhibiting or reducing maturation of TACE. TACE maturation can be detected and quantified by Western blotting. The iRhom2 referred to herein can be a mammalian iRhom2 or in a particular aspect, a human iRhom2, or a splice variant thereof.

The term "TACE", "ADAM17" or "ADAM metallopeptidase domain 17" refers to a protein having an amino acid sequence substantially identical to any of the representative TACE sequences of GenBank Accession Nos. NP_003174.3 (human), NP_033745.4 (mouse) and NP_064702.1 (rat). Suitable cDNA encoding TACE are provided at GenBank Accession Nos. NM_003183.4 (human), NM_009615.5 (mouse) and NM_020306.1 (rat).

Two forms of TACE are found in cells; a full-length precursor and a 100 kD mature form lacking the prodomain. Prodomain removal occurs in a late Golgi compartment, consistent with the proposed role of a furin type proprotein convertase in this process. An additional non-physiological form of TACE, lacking the pro and cytoplasmic domains, is detected when cell lysates are prepared in the presence of EDTA instead of a hydroxamate-based metalloprotease inhibitor or 1,10-phenanthroline. Mature TACE could be separated from and quantitated by Western blot, where it is the fastest migrating form of TACE McIllwein et al., *Science* 335.229 (2012) and Adrain et al., *Science* 335.225 (2012)).

TACE and iRhom1 are believed to bind together to form a complex and to co-immunoprecipitate. The ability of an agent to modulate (increase or decrease) binding between TACE and iRhom1 is believed to correlate with the ability of the agent to modulate the activity of iRhom1, and by extension, TACE. The amount of complex formation should be measurable by methods known in the art (as described in Adrain et al., *Science* 335.225 (2012) for iRhom2 and TACE), and include immunoprecipitation with tagged iRhom1 or tagged TACE. For example, the binding partners can be expressed in eukaryotic cell expression systems, and tested for antibodies or reagents that prevent binding, dissociate bound molecules, or stabilize the interaction, with, for example, pulldown assays, assays where one binding partner is immobilized on a plate and the second one is tagged and added. The quantity of the tagged molecule released into the supernatant can then be assessed by measuring the amount of released tagged protein by Western blot, dot blot or ELISA. An enzyme tag can be used, such as alkaline phosphatase, in which case the release can be measure by colorimetric determination of alkaline phosphatase activity in the supernatant A fluorescent protein tag can be added, in which case the release can be measure by a fluorimeter.

TACE and iRhom2 bind together to form a complex and can immunoprecipitate (Adrain et al., *Science* 335.225 (2012)). The ability of an agent to modulate (increase or decrease) binding between TACE and iRhom2 is disclosed herein to correlate with the ability of the agent to modulate the activity of iRhom2, and by extension, TACE. The amount of complex formation can be measured by methods known in the art (see Adrian et al., supra), and include immunoprecipitation with tagged iRhom2 or tagged TACE. For example, the binding partners can be expressed in eukaryotic cell expression systems, and tested for antibodies or reagents that prevent binding, dissociate bound molecules, or stabilize the interaction, with, for example, pulldown assays, assays where one binding partner is immobilized on a plate and the second one is tagged and added. The quantity of the tagged molecule released into the supernatant can then be assessed by measuring the amount of released tagged protein by Western blot, dot blot or ELISA. An enzyme tag can be used, such as alkaline phosphatase, in which case the release can be measure by colorimetric determination of alkaline phosphatase activity in the supernatant A fluorescent protein tag can be added, in which case the release can be measure by a fluorimeter.

Transforming growth factor α (TGFα) is a small 50 amino acid residue long mitogenic protein that contains three disulfide bridges. TGFα shares about 30% sequence identity with epidermal growth factor (EGF) and competes with EGF for the same membrane-bound receptor sites. High amounts of TGFα/EGF receptor complexes have been noticed in some human cancers. TGF as are secreted by human cancer cells and retrovirus-transformed fibroblasts.

A "biological equivalent" of a protein or nucleic acid refers to a protein or nucleic acid that is substantially identical to the protein or nucleic acid. As used herein, the term "substantially identical", when referring to a protein or polypeptide, is meant one that has at least 80%, 85%, 90%, 95%, or 99% sequence identity to a reference amino acid sequence. The length of comparison is preferably the full length of the polypeptide or protein, but is generally at least 10, 15, 20, 25, 30, 40, 50, 60, 80, or 100 or more contiguous amino acids. A "substantially identical" nucleic acid is one that has at least 80%, 85%, 90%, 95%, or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

In one aspect of any of the above methods, the agent that decreases the biological activity of iRohm 1 (or iRhom2) is an antibody or antibody fragment that specifically recognizes iRhom 1 (or iRhom2) and inhibits the activity of TACE; a small molecule inhibitor of iRhom1 (or iRhom2); a polypeptide decoy mimicking a domain necessary for the interaction of TACE and iRhom 1 (or iRhom2); a miRNA, a siRNA, a shRNA, a dsRNA or an antisense RNA directed to iRhom1 (or iRhom2) DNA or mRNA; a polynucleotide encoding the miRNA, siRNA, shRNA, dsRNA or antisense RNA; or an equivalent of each thereof. In another alternative, the agent that decreases the biological activity of iRhom1 or iRhom2 modulates (increases or decreases) formation of a complex between iRhom1 (or iRhom2) and TACE or inhibits the maturation of TACE.

In one aspect, the agent that decreases the biological activity of iRhom1 is an antibody or antibody fragment that specifically recognizes iRhom1 and inhibits the activity of TACE, or a polypeptide decoy mimicking a domain necessary for the interaction of TACE and iRhom1. In a particular aspect, the antibody or antibody fragment specifically recognizes an extracellular domain of iRhom1. For example, the antibody or antibody fragment recognizes and specifically binds to the polypeptide SAPDLAGNKRQFGS- VCHQDPRVCDEPSSEDPHEWPEDITKWPICTKSSAG (SEQ ID NO 5) or an antibody binding fragment thereof containing 5 to 10, 10 to 15, 15 to 20, 20-25, 25-30, 30-40, 40-45 or more than 45 amino acids. This polypeptide is a highly conserved fragment of the extracellular loop. Alternatively, the antibody or antibody fragment recognizes and specifically binds to a transmembrane region of iRhom2 or a region that includes both the extracellular loop and the transmembrane region. In another aspect, the agent further comprises a cell penetrating peptide. The cell penetrating peptide, in one aspect, comprises a HIV-TAT peptide.

In one aspect, the agent that decreases the biological activity of iRhom2 is an antibody or antibody fragment that specifically recognizes iRhom2 and inhibits the activity of TACE, or a polypeptide decoy mimicking a domain necessary for the interaction of TACE and iRhom2. In a particular aspect, the antibody or antibody fragment specifically recognizes an extracellular domain of iRhom2. For example, the antibody or antibody fragment recognizes and specifically binds to the polypeptide GPSDKSDLSQKQPSAV-VCHQDPRTCEEPASSGAHIWPDDITKWPICTEQAQS (SEQ ID NO 6) or an antibody binding fragment thereof containing 5 to 10, 10 to 15, 15 to 20, 20-25, 25-30, 30-40, 40-45 or more than 45 amino acids. This polypeptide is a highly conserved fragment of the extracellular loop. Alternatively, the antibody or antibody fragment recognizes and specifically binds to a transmembrane region of iRhom2 or a region that includes both the extracellular loop and the transmembrane region. In another aspect, the agent further comprises a cell penetrating peptide. The cell penetrating peptide, in one aspect, comprises a HIV-TAT peptide.

Agents which modulate the formation of a complex between iRhom1 and TACE include compounds that increase (e.g., stabilize) or decrease (e.g., destabilize or inhibit) the binding between the two proteins, resulting in more complex formation or less complex formation, respectively. Examples of agents that inhibit binding include an antibody or an antibody fragment that specifically recognizes the iRhom1 protein, and preferably the extracellular loop of either iRhom1 (the polypeptide SAPDLAGNKRQF-GSVCHQDPRVCDEPSSEDPHEWPEDITK-WPICTKSSAG (SEQ ID NO 5) or an antibody binding fragment thereof containing 5 to 10, 10 to 15, 15 to 20, 20-25, 25-30, 30-40, 40-45 or more than 45 amino acids. Alternatively, the antibody or antibody fragment that specifically recognizes a transmembrane domain of iRohm1 or a region comprising the extracellular domain and a transmembrane domain.

Agents which modulate the formation of a complex between iRhom2 and TACE include compounds that increase (e.g., stabilize) or decrease (e.g., destabilize or inhibit) the binding between the two proteins, resulting in more complex formation or less complex formation, respectively. Examples of agents that inhibit binding include an antibody or an antibody fragment that specifically recognizes the iRhom2 protein, and preferably the extracellular loop of either iRhom2 (the polypeptide GPSDKS-DLSQKQPSAVVCHQDPRTCEEPASSGAHIWPDDITK-WPICTEQAQS (SEQ ID NO 6) or an antibody binding fragment thereof containing 5 to 10, 10 to 15, 15 to 20, 20-25, 25-30, 30-40, 40-45 or more than 45 amino acids. Alternatively, the antibody or antibody fragment that specifically recognizes a transmembrane domain of iRhom1 or a region comprising the extracellular domain and a transmembrane domain.

In another alternative, the agent that inhibits binding is an antibody or antibody fragment that specifically recognizes the extracellular domain of either TACE (the polypeptide murine TACE accession number: www.ncbi.nlm.nih.gov/protein/NP_033745.4—the extracellular domain is between aa #1 and ~670; and human TACE accession number: www.ncbi.nlm.nih.gov/protein/NP_003174.3—the extracellular domain is between aa #1 and ~670) or an antibody binding fragment thereof containing 5 to 10, 10 to 15, 15 to 20, 20-25, 25-30, 30-40, 40-45 or more than 45 amino acids. In another alternative, the inhibitor of complex formation can be a small molecule which binds either iRhom1 (or iRhom2) or TACE in the region where the two proteins bind, e.g., a fragment of either protein which binds the other or a decoy that mimics a domain necessary for the interaction of TACE and iRhom1 (or iRhom2). This region can also include the transmembrane domain of TACE and one or more of the seven transmembrane domains of iRohm1 (or iRhom2). Agents which inhibit the formation of a complex between iRhom1 (or iRohm2) and TACE also include compounds which suppress the expression of iRohm2, e.g., iRNA can be a miRNA, a siRNA, a shRNA, a dsRNA or an antisense RNA directed to iRHom 1 (or iRhom2) DNA or mRNA, or a polynucleotide encoding the miRNA, siRNA, shRNA, dsRNA or antisense RNA, a vector comprising the polynucleotide. Agents that increase complex formation include antibodies or antibody fragments or small molecules that bind to and stabilize the complex. This would be identified from combinatorial chemistry inhibitor libraries by screens, and then further optimized through chemical alterations. In another aspect, the agent further comprises a cell penetrating peptide. The cell penetrating peptide, in one aspect, comprises a HIV-TAT peptide.

"Short interfering RNAs" (siRNA) refer to double-stranded RNA molecules (dsRNA), generally, from about 10 to about 30 nucleotides in length that are capable of mediating RNA interference (RNAi). "RNA interference" (RNAi) refers to sequence-specific or gene specific suppression of gene expression (protein synthesis) that is mediated by short interfering RNA (siRNA). As used herein, the term siRNA includes short hairpin RNAs (shRNAs). A siRNA directed to a gene or the mRNA of a gene may be a siRNA that recognizes the mRNA of the gene and directs a RNA-induced silencing complex (RISC) to the mRNA, leading to degradation of the mRNA. A siRNA directed to a gene or the mRNA of a gene may also be a siRNA that recognizes the mRNA and inhibits translation of the mRNA. A siRNA may be chemically modified to increase its stability and safety. See, e.g. Dykxhoorn and Lieberman (2006) Annu. Rev. Biomed. Eng. 8:377-402 and U.S. Patent Application Publication No.: 2008/0249055.

"Double stranded RNAs" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

"MicroRNAs" (miRNA) refer to single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

siRNA, dsRNA, and miRNA to inhibit gene expression can be designed following procedures known in the art. See, e.g., Dykxhoorn and Lieberman (2006) Annu. Rev. Biomed. Eng. 8:377-402; Dykxhoorn et al. (2006) Gene Therapy 13:541-52; Aagaard and Rossi (2007) Adv. Drug Delivery Rev. 59:75-86; de Fougerolles et al. (2007) Nature Reviews Drug Discovery 6:443-53; Krueger et al. (2007) Oligonucleotides 17:237-250; U.S. Patent Application Publication No.: 2008/0188430; and U.S. Patent Application Publication No.: 2008/0249055.

Delivery of siRNA, dsRNA or miRNA to a cell can be made with methods known in the art. See, e.g., Dykxhoorn and Lieberman (2006) Annu. Rev. Biomed. Eng. 8:377-402; Dykxhoorn et al. (2006) Gene Therapy 13:541-52; Aagaard and Rossi (2007) Adv. Drug Delivery Rev. 59:75-86; de Fougerolles et al. (2007) Nature Reviews Drug Discovery 6:443-53; Krueger et al. (2007) Oligonucleotides 17:237-250; U.S. Patent Application Publication No.: 2008/0188430; and U.S. Patent Application Publication No.: 2008/0249055.

"Antisense" oligonucleotides have nucleotide sequences complementary to the protein coding or "sense" sequence. Antisense RNA sequences function as regulators of gene expression by hybridizing to complementary mRNA sequences and arresting translation (Mizuno et al. (1984) PNAS 81:1966; Heywood et al. (1986) Nucleic Acids Res. 14:6771). An antisense polynucleotide comprising the entire sequence of the target transcript or any part thereof can be synthesized with methods known in the art. See e.g., Ferretti et al. (1986) PNAS 83:599. The antisense polynucleotide can be placed into vector constructs, and effectively introduced into cells to inhibit gene expression (Izant et al. (1984) Cell 36:1007). Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the gene is retained as a functional property of the polynucleotide.

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provide desirable properties (e.g., increased nuclease-resistance, tighter-binding, stability or a desired $T_m$). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al. (1991) Science 254:1497) or incorporating 2'-O-methyl ribonucleotides, phosphorothioate nucleotides, methyl phosphonate nucleotides, phosphotriester nucleotides, phosphorothioate nucleotides, phosphoramidates. Another example of the modification is replacement of a non-bridging phosphoryl oxygen atom with a sulfur atom which increases resistance to nuclease digestion. Increased antisense polynucleotide stability can also be achieved using molecules with 2-methyoxyethyl substituted backbones. See e.g., U.S. Pat. Nos. 6,451,991 and 6,900,187.

In another embodiment, ribozymes can be used (see, e.g., Cech (1995) Biotechnology 13:323; and Edgington (1992) Biotechnology 10:256 and Hu et al., PCT Publication WO 94/03596). A ribonucleic acid enzyme ("ribozymes", "RNA enzyme", or "catalytic RNA") is an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome. Methods of making and using ribozymes can be found in e.g., U.S. Patent Application Publication No. 2006/0178326.

"Triplex ribozymes" configurations allow for increased target cleavage relative to conventionally expressed ribozymes. Examples of triplex ribozymes include hairpin ribozymes and hammerhead ribozymes. Methods of making and using triplex ribozymes are found in, e.g., Aguino-Jarguin et al. (2008) Oligonucleotides 18(3):213-24 and U.S. Patent Application Publication No. 2005/0260163.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz (1996) Current Opinion in Neurobiology 6:629-634. Another subsequence, the h (hydrophobic) domain of signal peptides, was found to have similar cell membrane translocation characteristics (see, e.g., Lin et al. (1995) J. Biol. Chem. 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

The present disclosure provides, in one embodiment, a polypeptide decoy that mimics a domain necessary for the interaction of TACE and iRhom1 (or iRhom2) for decreasing the biological activity of iRhom1 (or iRhom2). A polypeptide decoy of a protein for inhibiting the interaction between the protein and a second protein is a polypeptide that binds to the second protein but does not carry out the biological activity that such a binding would normally carry out.

In one embodiment, a polypeptide decoy is a fragment of the iRhom1 (or iRhom2) protein that includes the iRhom 1 (or iRhom2) extracellular domain responsible for binding TACE, e.g., a polypeptide with the amino sequence of SEQ ID NO 3, 4, 5 or 6 or a 5 to 10, 10 to 15, 15 to 20, 20-25, 25-30, 30-40, 40-45 or more than 45 amino acid fragment thereof that binds TACE. In another embodiment, the polypeptide decoy does not include an iRhom1 (or iRhom2) domain that is responsible for activating TACE or contains a mutation at this domain so that the polypeptide decoy does not activate TACE. Alternatively, the polypeptide decoy also includes a portion of the transmembrane domain of iRhom1 (or iRhom2), together with or in the absence of the extracellular domain.

In another embodiment, a polypeptide decoy is a fragment of the TACE protein that includes the TACE extracellular domain responsible for binding iRhom2, e.g., or a 5 to 10, 10 to 15, 15 to 20, 20-25, 25-30, 30-40, 40-45 or more than 45 amino acid fragment thereof that binds with iRohm2. In another embodiment, the polypeptide decoy does not include a TACE domain that is responsible for its shedding activity or contains a mutation at this domain so that the polypeptide decoy does not have shedding activity. Alternatively, the polypeptide decoy also includes a portion of the transmembrane domain of TACE together with or in the absence of a portion of the extracellular domain of TACE.

"Antibody" is intended to encompass both polyclonal and monoclonal antibodies. The terms polyclonal and monoclonal refer to the degree of homogeneity of an antibody preparation, and are not intended to be limited to particular methods of production. "Antibody" also encompasses functional fragments of antibodies, including fragments of chimeric, humanized, primatized, veneered or single chain antibodies. For example, an antibody can be an IgG or antigen-binding fragment of an IgG. Antibody fragments include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain fragment can be designed to include DNA sequences encoding the CH, domain and hinge region of the heavy chain.

Single chain antibodies, and chimeric, humanized or primatized (CDR-grafted), or veneered antibodies, as well as chimeric, CDR-grafted or veneered single chain antibodies, comprising fragments derived from different species, and the like are also encompassed by the term "antibody". The various fragments of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for a mammalian (e.g., human) specific portion of iRhom1 (or iRohm2) and TACE that affect binding between the two proteins or which inhibit a biological activity of iRohm1 and iRohm2 can be raised against an appropriate immunogen, such as isolated and/or recombinant extracellular loop of iRohm 1 or iRohm2 or the extracellular domain of TACE, with or without the transmembrane domains attached, or fragments thereof (including synthetic molecules, such as synthetic peptides).

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977), Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody producing cells. Antibody producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library), or which rely upon immunization of transgenic animals (e.g., mice) capable of producing a repertoire of human antibodies (see e.g., Jakobovits et al., Proc. Natl. Acad. Sci. USA, 90: 2551-2555 (1993); Jalkobovits et al., Nature, 362: 255-258 (1993); Lonberg et al., U.S. Pat. No. 5,545,806; Surani et al., U.S. Pat. No. 5,545,807; Lonberg et al., WO97/13852).

In one embodiment, the antibody or antigen-binding fragment used in the disclosed methods binds to a fragment of the extracellular loop of iRhom1, iRohm2 or TACE. The fragment can be 5 to 10 amino acids long, 10 to 15 amino acids long, 15 to 20 amino acids long, 20-25 amino acids long, 25-30 amino acids long, 30-35 amino acids long, 35-40 amino acids long, 40-45 amino acids long or greater than 45 amino acids long.

The agent that decreases the biological activity of iRhom1 and the agent that decreases the biological activity of iRhom2 can be different compounds. Alternatively, the agent that decreases the biological activity of iRhom1 and the agent that decreases the biological activity of iRhom2 can be the same compound. For example, as shown in FIG. 3, there is substantial homology between the amino acid sequence of the extracellular loop of iRhom1 and iRhom2. Therefore, it is believed that antibodies which bind both extracellular loops and that decrease a biological activity of both iRhom1 and iRhom2 can be generated. Similarly, it should be possible to generate polypeptide decoys based on the amino acid sequences of the extracellular loop of iRhom1 and iRhom2 that bind TACE in such a manner so as to inhibit a biological activity of both iRohm1 and iRhom2.

The compositions described herein for a therapeutic use may be administered with an acceptable pharmaceutical carrier. Acceptable "pharmaceutical carriers" are well known to those of skill in the art and can include, but not be limited to any of the standard pharmaceutical carriers, such as phosphate buffered saline, water and emulsions, such as oil/water emulsions and various types of wetting agents.

The term "treating" is meant administering a pharmaceutical composition for the purpose of therapeutic treatment by reducing, alleviating or reversing at least one adverse effect or symptom.

The term "administering" for in vivo and ex vivo purposes means providing the subject with an effective amount of the nucleic acid molecule or polypeptide effective to prevent or inhibit a disease or condition in the subject. Methods of administering pharmaceutical compositions are well known to those of skill in the art and include, but are not limited to, microinjection, intravenous or parenteral administration. The compositions are intended for systemic, topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician. For example, the compositions can be administered prior to a subject already suffering from a disease or condition that is linked to apoptosis.

The term "effective amount" refers to a quantity of compound (e.g., an agent that decreases the biological activity of iRhom1 or iRhom2 or that modulates (increases or decreases) formation of a complex between iRhom1 (or iRhom2) and TACE) delivered with sufficient frequency to provide a medical benefit to the patient. In one embodiment, an effective amount of a protein is an amount sufficient to treat or ameliorate a symptom of an EGFR dependent pathology. Exemplary effective amounts of agent that decreases the biological activity of iRhom1 (or iRhom2) or that modulates (increases or decreases) formation of a complex between iRhom1 (or iRhom2) and TACE range from 0.1 ug/kg body weight to 100 mg/kg body weight; alternatively 1.0 ug/kg body weight to 10 mg/kg body weight An inhibitor of a biological activity of iRhom 1 and an inhibitor of a biological activity of iRhom 2 can be used alone or a combination with another anticancer agent. Anti-cancer agents that are commonly combined with the disclosed methods include platinum based chemotherapy. Platinum chemotherapy is the term for treatment with one of the chemotherapy drugs that contain derivatives of the metal platinum. The platinum damages the DNA of the cancer cells.

Exemplary platinum based anticancer agents include Cisplatin, carboplatin, capecitabine and oxaliplatin.

A "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

The invention also includes a method of identifying an agent to be used in combination with an agent that inhibits a biological activity of iRhom 2 (or iRhom1) for the treatment of an EGFR dependent pathology. The method assesses the ability of a test agent to modulate (increase or decrease) complex formation between iRhom1 (or iRhom2) and TACE. The method comprises the step of combining TACE, iRhom1 (or iRhom2) and a test agent under conditions suitable for forming a complex between TACE and iRhom1 (or iRhom2). This could be a pre-existing complex of iRhom1 (or iRhom2) and TACE that is immunoprecipitated from cells, such as myeloid cells to assess the interaction between iRhom2 and TACE; and keratinocytes or fibroblasts to assess the interaction between iRhom1 and TACE. It could also be a complex of recombinantly expressed extracellular loop of iRhom1 (or iRhom2) and extracellular domain of TACE, with tags added, as described above. The amount of complex formation is compared to the amount of complex formed under identical conditions in the absence of the test agent. A greater or lesser amount of complex formation in the presence of the test agent than in its absence is indicative that test agent is effective for the treatment of an EGFR mediated pathology. Methods for assessing complex formation between iRhom 2 and TACE are provided in Adrain et al., *Science* 335.225 (2012).

The efficacy a test agent showing the ability to modulate complex formation between iRhom 1 (or iRohm2) and TACE can be further tested and/or confirmed in additional assays for assessing efficacy against any one or more disease mediated by an EGFR dependent pathology. Typically, a plurality of test agents are tested, for example as in high throughput screening, for their ability to modulate complex formation between iRhom1 (or iRhom2) TACE. Those test agents demonstrating an ability to modulate complex formation between iRhom1 (or iRhom2) and TACE are typically selected for further testing in assays for assessing efficacy against any one or more EGFR dependent pathologies.

An alternative method for identifying an agent which can be used in combination with an inhibitor of a biological activity of iRhom2 for the treatment of an EGFR dependent pathology assesses the ability of a test agent to inhibit release an EGFR ligand. Exemplary EGFR ligands include TGFα, HB-EGF, amphiregulin, epiregulin and epigen. The method comprises combining a cell that releases an EGFR ligand (e.g., a mouse embryonic fibroblast, keratinocyte or endothelial cell) and a test agent under conditions suitable for stimulating TGFα release. The cell is either iRhom2–/–; or an inhibitor of iRhom 2 is additionally combined with the cell and test agent.

An alternative method for identifying an agent which can be used in combination with an inhibitor of a biological activity of iRhom1 for the treatment of an EGFR dependent pathology assesses the ability of a test agent to inhibit release an EGFR ligand. Exemplary EGFR ligands include TGFα, HB-EGF, amphiregulin, epiregulin and epigen. The method comprises combining a cell that releases of an EGFR ligand (e.g., a mouse embryonic fibroblast, keratinocyte or endothelial cells) and a test agent under conditions suitable for stimulating TGFα release. The cell is either iRhom1−/−; or an inhibitor of iRhom 1 is additionally combined with the cell and test agent.

Exemplary conditions for carrying out the assay described in the previous two paragraphs and measuring the quantities of TGFα released by a cell are provided in Sahin et al., "Distinct Roles for ADAM10 and ADAM 17 in Ectodomain Shedding of six EGFR Ligands" The Journal of Cell Biology, 164:769 (2004); Sahin, et al., "Ectodomain shedding of the EGF-Receptor Ligand Epigen is Mediated by ADAM17", FEBS, 581:41 (2007); Le Gall, et al., "ADAMs 10 and 17 Represent Differentially Regulated Components of a General Shedding Machinery for Membrane Proteins Such as Transforming Growth Factor α, L-Selectin, and Tumor Necrosis Factor α", Molecular Biology of the Cell, 20:1785 (2009); Le Gall, et al., "ADAM 17 is Regulated by a Rapid and Reversible Mechanism that Controls Access to its Catalytic Site", Journal of Cell Science, 123:3913 (2010). For example, EGFR-ligand release can be measured by ELISA for TGFα, for example, or HB-EGF, or by release of tagged EGFR ligands. They can be tagged with alkaline phosphatase or any other tag that facilitates detection of the released growth factor into the supernatant. The quantity of EGFR ligand release is measured and compared with the quantity released under identical conditions in the absence of the test agent. Diminished EGFR ligand release in the presence of the test agents than in its absence is indicative of a test agent useful for the treatment of an EGFR dependent pathology. The efficacy of a test agent showing the ability to inhibit EGFR ligand release for treating EGFR dependent pathologies can be further tested and/or confirmed in additional assays for assessing efficacy against any one or more EGFR dependent pathologies. Typically, a plurality of test agents are tested, for example as in high throughput screening, for their ability to inhibit EGFR ligand release. Those test agents demonstrating an ability to inhibit EGFR ligand release are typically selected for further testing in assays for assessing efficacy against any one or more EGFR mediated pathology.

Another method for identifying an agent which can be used in combination with an inhibitor of a biological activity of iRhom1 for the treatment of an EGFR dependent pathology assesses the ability of a test agent to inhibit maturation of the 100 kD form of TACE, i.e., inhibits expression of the mature 100 kD form of TACE. The method comprises the step of combining the test agent and a cell which expresses the mature 100 kD form of TACE (e.g., on reducing SDS-PAGE) under conditions suitable for the expression of the mature form of TACE. Exemplary cells which express the mature form of TACE include Cos7 cells, mEF cells, endothelial cells, keratinocytes and many other cell types (because TACE is ubiquitously expressed). The cell is either iRhom1−/−; or an inhibitor of iRhom 1 is additionally combined with the cell and test agent.

Another method for identifying an agent which can be used in combination with an inhibitor of a biological activity of iRhom2 for the treatment of an EGFR dependent pathology assesses the ability of a test agent to inhibit maturation of the 100 kD form of TACE, i.e., inhibits expression of the mature 100 kD form of TACE. The method comprises the step of combining the test agent and a cell which expresses the mature 100 kD (e.g., on reducing SDS-PAGE) form of TACE under conditions suitable for the expression of the mature form of TACE (e.g., on reducing SDS-PAGE). Exemplary cells which express the mature form of TACE include Cos7 cells, mEF cells, endothelial cells, keratinocytes and many other cell types (because TACE is ubiquitously expressed). The cell is either iRhom2−/−; or an inhibitor of iRhom2 is additionally combined with the cell and test agent.

The quantity of mature TACE that is expressed can be assessed using techniques known to one skilled in the art, e.g., Western blotting (e.g., on reducing SDS-PAGE). The quantity of mature TACE expression is measured and compared with the quantity produced under identical conditions in the absence of the test agent. Diminished expression of mature TACE in the presence of the test agents than in its absence is indicative of a test agent useful for the treatment of an EGFR dependent pathology. The efficacy of a test agent showing the ability in combination with an inhibitor of iRhom1 or iRhom2 to inhibit EGFR ligand release for treating EGFR dependent pathologies can be further tested and/or confirmed in additional assays for assessing efficacy against any one or more EGFR dependent pathologies. Typically, a plurality of test agents are tested, for example as in high throughput screening, for their ability to inhibit EGFR ligand release in combination with an inhibitor of iRhom1 or iRhom2. Those test agents demonstrating an ability to inhibit EGFR ligand release in combination with an inhibitor of iRhom1 or iRhom2 are typically selected for further testing in assays for assessing efficacy against any one or more EGFR mediated pathology.

Assays for assessing efficacy of a test agent against one or more diseases EGFR dependent pathologies are well known in the art.

What is claimed is:

1. A method of identifying an agent which can be used in combination with an inhibitor of a biological activity of iRhom1, which inhibitor binds to iRhom1 protein or to a polynucleotide encoding iRhom1 protein, for the treatment of an EGFR dependent pathology, wherein the biological activity is determined by measuring maturation of TACE and the inhibitor of the biological activity inhibits or reduces the maturation of TACE; wherein the EGFR dependent pathology is a disease that is caused by overexpression of EGER or aberrant activity of EGFR, wherein the aberrant activity of EGFR is caused by overexpression or increased release of an EGFR ligand; wherein the iRhom1 protein has an amino acid sequence at least 95% identical to the iRhom1 sequence of GenBank Accession No. NP_071895.3 or NP_034247.2, comprising the steps of:
   a) combining a test agent and a cell which releases an EGFR ligand under conditions suitable for stimulating release of the EGFR ligand, wherein the cell is iRhom1−/− or wherein an effective amount of an inhibitor of the biological activity of iRhom1 is additionally combined with the cell and test agent;
   b) assessing the quantity of released EGFR ligand, wherein diminished EGFR ligand release in the presence of the test agent compared to in the absence is indicative that the test agent is useful in combination with an inhibitor of the biological activity of iRhom1 for the treatment of an EGFR dependent pathology;
   c) optionally repeating steps a) and b) one or more times with a different test agent;
   d) selecting the test agent(s) for which the amount of EGFR ligand release is diminished in the presence of the test agent compared to in the absence of the test agent; and
   e) assaying the test agent(s) selected in step d) in combination with an inhibitor of the biological activity of iRhom1 in an assay for testing the efficacy against an EGFR dependent pathology.

2. The method of claim 1, wherein the EGFR ligand is TGF-α and the cell is mouse embryonic fibroblast.

3. A method of identifying an agent which can be used in combination with an inhibitor of a biological activity of iRhom2, which inhibitor binds to iRhom2 protein or to a polynucleotide encoding iRhom2 protein, for the treatment of an EGFR dependent pathology, wherein the biological activity is determined by measuring maturation of TACE and the inhibitor of the biological activity inhibits or reduces the maturation of TACE; wherein the EGFR dependent pathology is a disease that is caused by overexpression of EGER or aberrant activity of EGFR, wherein the aberrant activity of EGFR is caused by overexpression or increased release of an EGFR ligand; wherein the iRhom2 protein has an amino acid sequence at least 95% identical to the iRhom2 sequence of GenBank Accession No. NP_001005498.2, NP_078875.4 or NP_001161152.1, comprising the steps of:
   a) combining a test agent and a cell which releases an EGFR ligand under conditions suitable for stimulating release of the EGFR ligand, wherein the cell is iRhom2−/− or wherein an effective amount of an inhibitor of the biological activity of iRhom2 is additionally combined with the cell and test agent;
b) assessing the quantity of released EGFR ligand, wherein diminished EGFR ligand release in the presence of the test agent compared to in the absence is indicative that the test agent is useful in combination with an inhibitor of the biological activity of iRhom2 for the treatment of an EGFR dependent pathology;
c) optionally repeating steps a) and b) one or more times with a different test agent;
d) selecting the test agent(s) for which the amount of EGFR ligand release is diminished in the presence of the test agent compared to in the absence of the test agent; and
e) assaying the test agent(s) selected in step d) in combination with an inhibitor of the biological activity of iRhom2 in an assay for testing the efficacy against an EGFR dependent pathology.

4. The method of claim 3, wherein the EGFR ligand is TGF-α and the cell is mouse embryonic fibroblast.

* * * * *

UNITED STATES PATENT AND TRADEMARK OFFICE
CERTIFICATE OF CORRECTION

PATENT NO. : 10,024,844 B2
APPLICATION NO. : 14/654139
DATED : July 17, 2018
INVENTOR(S) : Carl Blobel et al.

It is certified that error appears in the above-identified patent and that said Letters Patent is hereby corrected as shown below:

In the Specification

At Column 1, Line numbers 15-17, delete "The research reported herein was supported in part by grant number NIH R01 GM64750. The Government has certain rights in the invention." and replace with --This invention was made with government support under Grant No. GM064750 awarded by the National Institutes of Health. The government has certain rights in the invention.--

Signed and Sealed this
Twenty-fourth Day of December, 2019

Andrei Iancu
*Director of the United States Patent and Trademark Office*